(12) United States Patent
Pierce et al.

(10) Patent No.: US 6,371,966 B1
(45) Date of Patent: Apr. 16, 2002

(54) CORNEAL INCISION DEVICE

(75) Inventors: Robert W. Pierce, Wrentham; Joseph F. Keenan, Cohasset; Dana Michael Cote, Saugus; Edwin G. Lee, Burlington, all of MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/500,598

(22) Filed: Feb. 10, 2000

Related U.S. Application Data

(63) Continuation-in-part of application No. 09/163,964, filed on Sep. 30, 1998, now Pat. No. 6,090,119.

(51) Int. Cl.⁷ .................................................. A61F 9/00
(52) U.S. Cl. ........................ 606/166; 606/107; 606/167; 604/22
(58) Field of Search ................................ 606/107, 166, 606/167, 185, 170, 171, 184; 604/19, 22

(56) References Cited

U.S. PATENT DOCUMENTS

| 4,205,682 A | * | 6/1980 | Crock et al. ................. 606/166 |
| 4,796,623 A | | 1/1989 | Krasner et al. |
| 4,844,060 A | | 7/1989 | Krumeich |
| 5,290,301 A | | 3/1994 | Lieberman ................... 606/166 |
| 5,486,188 A | | 1/1996 | Smith .......................... 606/166 |
| 5,571,124 A | | 11/1996 | Zelman ....................... 606/166 |
| 5,586,980 A | | 12/1996 | Kremer et al. |
| 5,611,805 A | | 3/1997 | Hall ............................ 606/166 |
| 5,779,723 A | | 7/1998 | Schwind ..................... 606/166 |
| 5,876,415 A | | 3/1999 | Pierce et al. ................ 606/166 |

* cited by examiner

Primary Examiner—Glenn K. Dawson
(74) Attorney, Agent, or Firm—Alan W. Fiedler

(57) ABSTRACT

A corneal incision device of the present invention includes a surgical blade and a frame having an inner surface with a configuration that is generally in the shape of a ring-like segment of a hollow sphere. The frame has an aperture therein to allow the surgical blade to be inserted through the frame beyond the inner surface. The aperture is sized and shaped to allow movement of the surgical blade in one axis. The device may have a protuberance affixed to the inner surface of the frame adjacent to the aperture disposed to distort a surface of a patient's eye when the device is selectively positioned on the eye by a practitioner. The device has provisions for holding, advancing and withdrawing the surgical blade through the aperture, disposed on the frame. The device is releasably retained on the patient's eye by fixation elements disposed on the inner surface of the frame. There is a handle affixed to the frame to facilitate the practitioner's manipulation of device.

14 Claims, 23 Drawing Sheets

US 6,371,966 B1

CORNEAL INCISION DEVICE

This application is a continuation-in-part of a previous filed patent application Ser. No. 09/163,964 filed on Sep. 30, 1998, now U.S. Pat. No. 6,090,119.

FIELD OF INVENTION

The present invention relates to surgical scalpels and more particularly to a device for making a precise incision in the eye of a patient.

BACKGROUND

Generally in surgical procedures, a practitioner makes an incision in the body of a patient in order to repair damaged tissue, modify tissue, remove tissue or to insert some sort of implantable device. Many procedures are combinations of these procedures. One example of such a combination is found in cataract surgery. Cataract surgery is performed to remove the lens of a patient's eye that has become substantially or partially opaque having an adverse effect on the patient's visual acuity. Practitioners have found that if the opacified lens is removed and replaced with an implantable intraocular lens (IOL), there are significant improvements in the patient's visual acuity. In order to perform this procedure, the practitioner makes an incision in the patient's eye sufficient to remove the non-functional lens and insert an appropriate IOL. The incision to facilitate the removal and replacement of the lens is made in the cornea or sclera of the eye. The incision provides the practitioner with access to the lens so that it may be removed.

There are a number of different procedures that are used to remove a non-functional lens from the eye, the most commonly practiced are referred to as extracapsular surgery and phacoemulsification. In extracapsular surgery, the practitioner removes the lens while allowing the posterior lens capsule to remain. In phacoemulsification, the practitioner reduces the lens to an emulsion by careful application of ultrasonic energy coupled with irrigation and suction, thereby removing the non-functional lens. In both of these procedures, the removed lens is then replaced by a synthetic polymeric IOL substantially restoring the visual acuity of the eye.

A critical component of this procedure is the incision that provides the practitioner with access to the non-functional natural lens so that it can be removed. The ideal incision for a lens removal and replacement is of a minimum size and accurately placed. The incision through which the several instruments used to conduct the procedure is preferably an opening substantially the same circumference as the instruments. Accurate sizing minimizes trauma to the eye and facilitates healing of the eye after the procedure is completed. In the case of the phacoemulsion procedure, if the incision is too small, corneal tissue adjacent the incision may be damaged by contact with the ultrasonic probe and alternatively, if the incision is too large, leakage from the eye may cause prolapse and loss of endothelial cells.

Another problem related to the incision in cataract surgery is suture induced astigmatism. An incision made in the eye must be closed after the procedure so that healing occurs and that there is no path for infection. Previously, sutures have been used to close the incision. A suture may alter the shape of the eye and result in astigmatism. Additionally, sutures may cause irritation, provide a location for infection and abscess or a foreign body reaction. Recently, sutureless techniques have been devised that allow the practitioner to make an incision of a particular shape or geometry that utilize the internal pressure in the eye to keep the incision closed until it heals without the use of sutures. Making such an accurately placed and sized incision for such a procedure is very technique sensitive. Apparatus and methods for making a properly sized and shaped incision for cataract removal procedures are available, but are still subject to variations in technique. If a device that made a practitioner's placement and sizing of an incision in the eye less technique sensitive, the art of eye surgery would be advanced. Such a device and a method for its use is disclosed hereinbelow.

SUMMARY

A corneal incision device of the present invention includes a surgical blade and a frame having an inner surface with a configuration that is generally in the shape of a ring-like segment of a hollow sphere. The frame has an aperture therein to allow the surgical blade to be inserted through the frame beyond the inner surface. The aperture defines a longitudinal axis and is sized and shaped to allow movement of the surgical blade in the longitudinal axis. The device has provisions for holding, advancing and withdrawing the surgical blade through the aperture, disposed on the frame. The device is releasably retained on the patient's eye by fixation elements disposed on the inner surface of the frame. There is a grip affixed to the frame to facilitate the practitioner's manipulation of device.

The device of the invention allows the practitioner to achieve a correct placement and precise shape for the desired incision. Once the practitioner has selectively positioned the device on the patient's eye, the surgical blade is correctly positioned and ready for selective activation by the practitioner. A further benefit of the blade placement provision is that the sharp blade is kept in a protected position until its use is desired by the practitioner. The device of the invention represents an improvement in the practitioner's ability to form, rapidly and correctly, a selectively precisely shaped incision in the patient's eye thereby improving the efficiency of a widely practiced and difficult procedure.

A corneal device for eye surgery of the present invention also includes a frame having a top, a bottom, and a side. The frame defines an aperture therein and has a hole to access the eye. A blade is supported by the frame and positioned at a fixed angle relative to the frame. An actuator is attached to the blade for advancing and withdrawing the blade in the fixed position through the aperture. By advancing the blade, an incision is created on the eye at the fixed angle on the blade. The blade can further withdraw back through the aperture of the frame.

DETAILED DESCRIPTION

Figure 1:
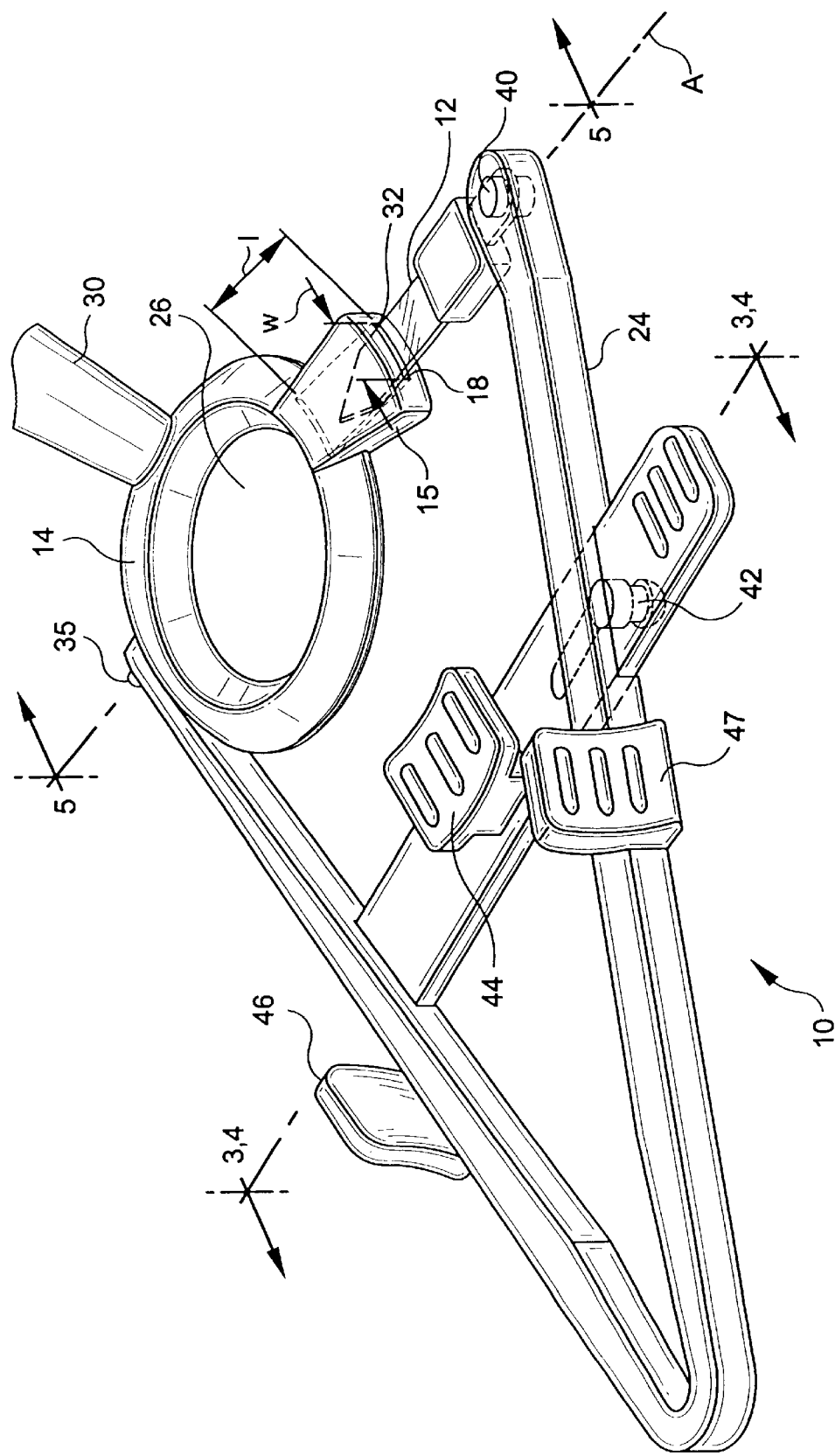
FIG. 1 is a perspective view of a preferred embodiment of the multiplane corneal incision device of the invention.
Figure 2:
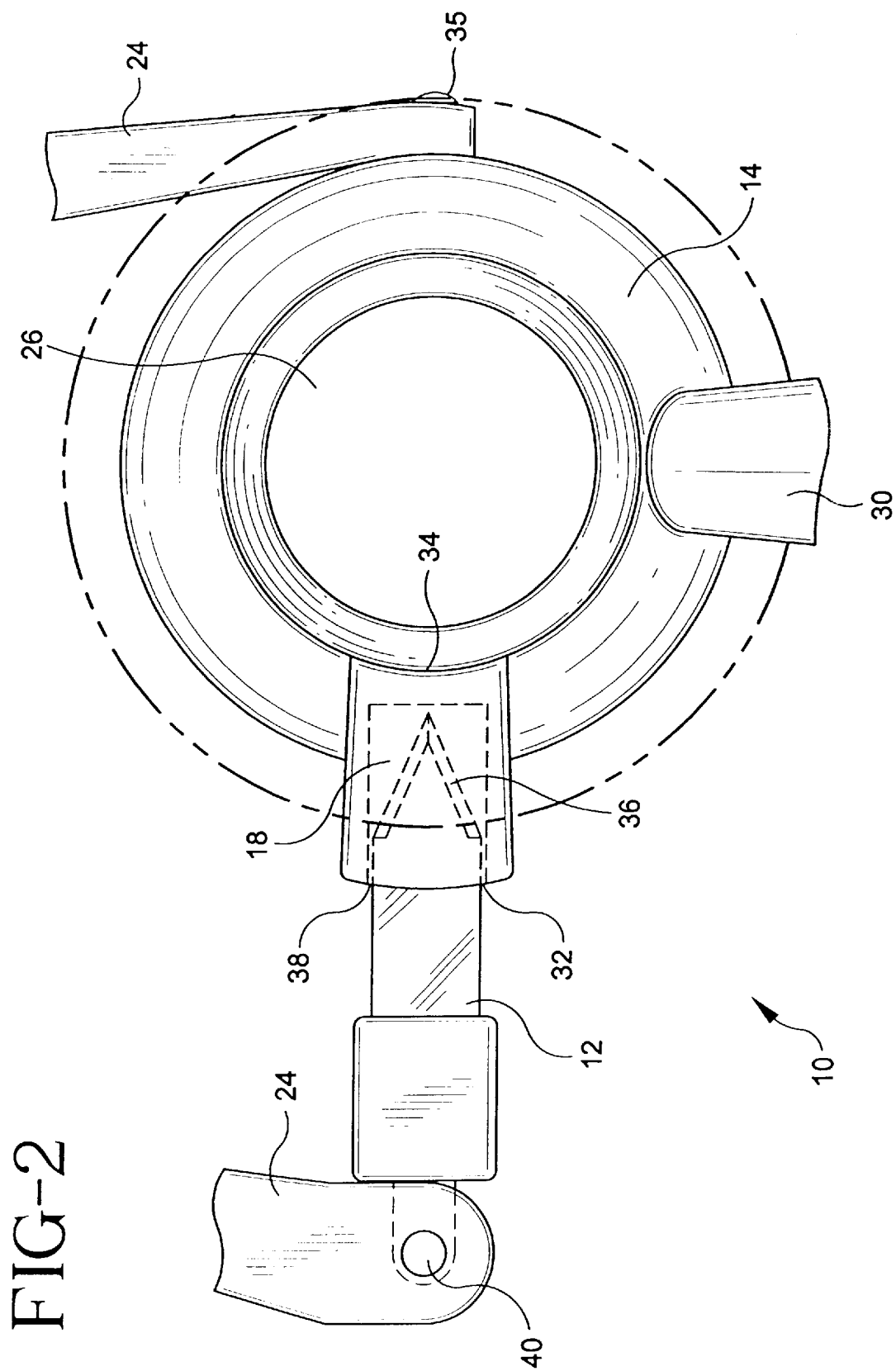
FIG. 2 is a partial top plan view of the device of FIG. 1.
Figure 3:
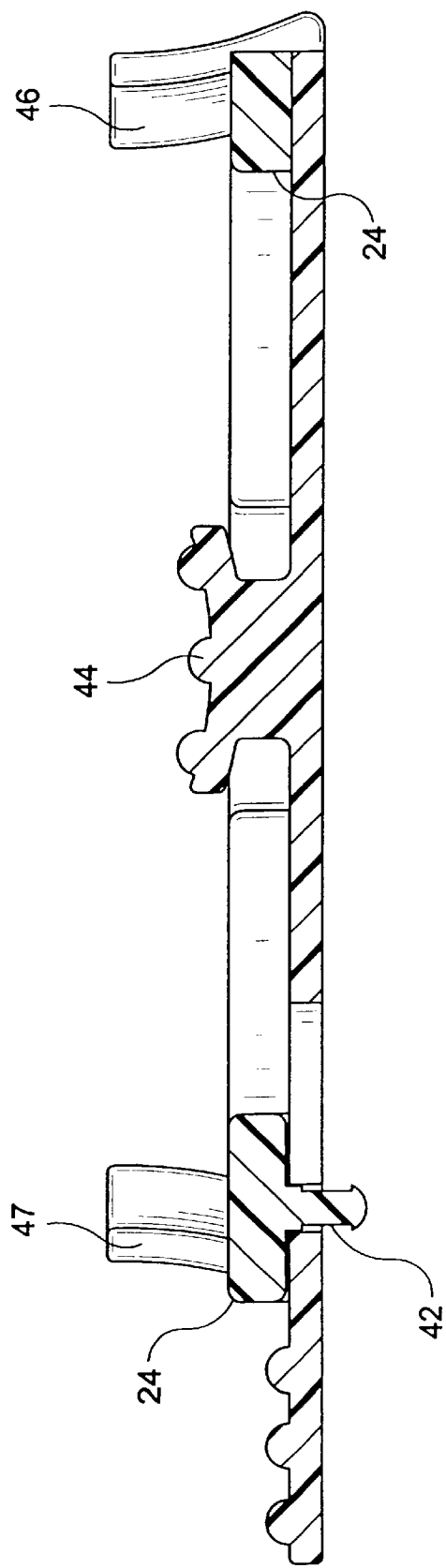
FIG. 3 is a cross-sectional view of the device of FIG. 1, along the line 3—3 with the latch in the first position.
Figure 4:
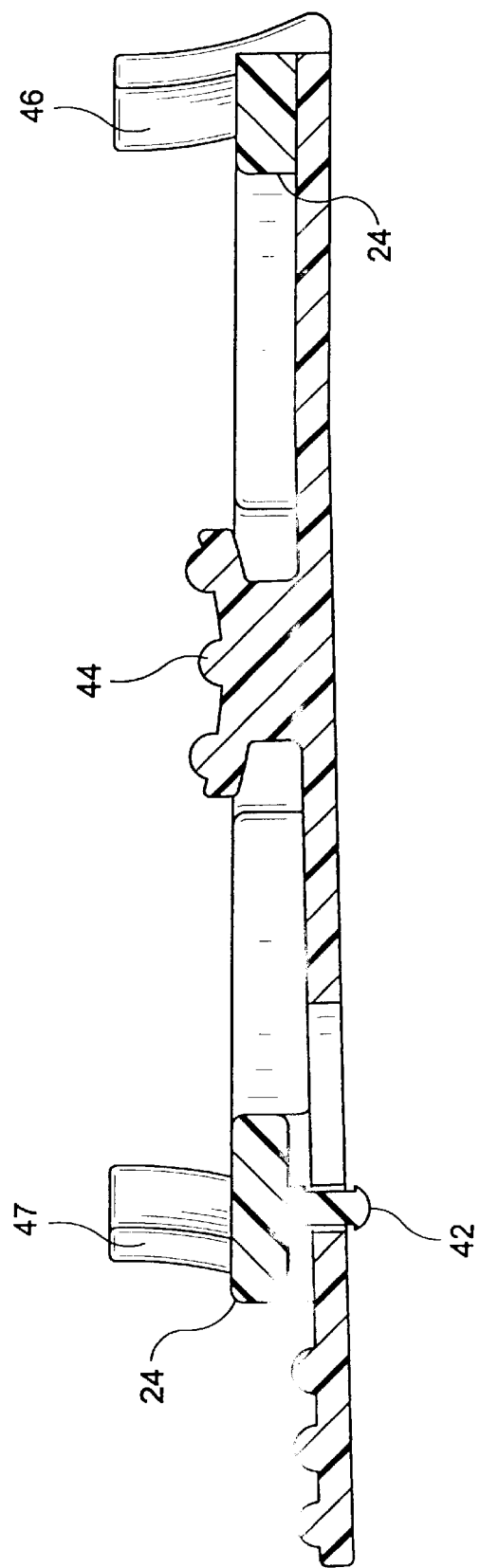
FIG. 4 is a cross-sectional view of the device of FIG. 1, analogous to FIG. 3, with the latch in the second position.

While this invention is satisfied by embodiments in many different forms, there is shown in the drawings and herein described in detail preferred embodiments of the invention with the understanding that the present disclosure is to be considered exemplary of the principles of the invention and is not intended to limit the invention to the embodiments illustrated. The scope of the invention is measured by the appended claims and their equivalents.

Referring to FIGS. 1–7, a corneal incision device 10 of the present invention includes a surgical blade 12, a frame 14 having an inner surface 16 with a configuration that is generally in the shape of a ring-like segment of a hollow sphere. Frame 14 defines an aperture 18 therein, preferably within a projecting portion 15, to allow surgical blade 12 to be inserted through frame 14 beyond inner surface 16. Aperture 18 defines an axis A, is sized and shaped to allow movement of surgical blade 12 in substantially only one axis.

Figure 6:
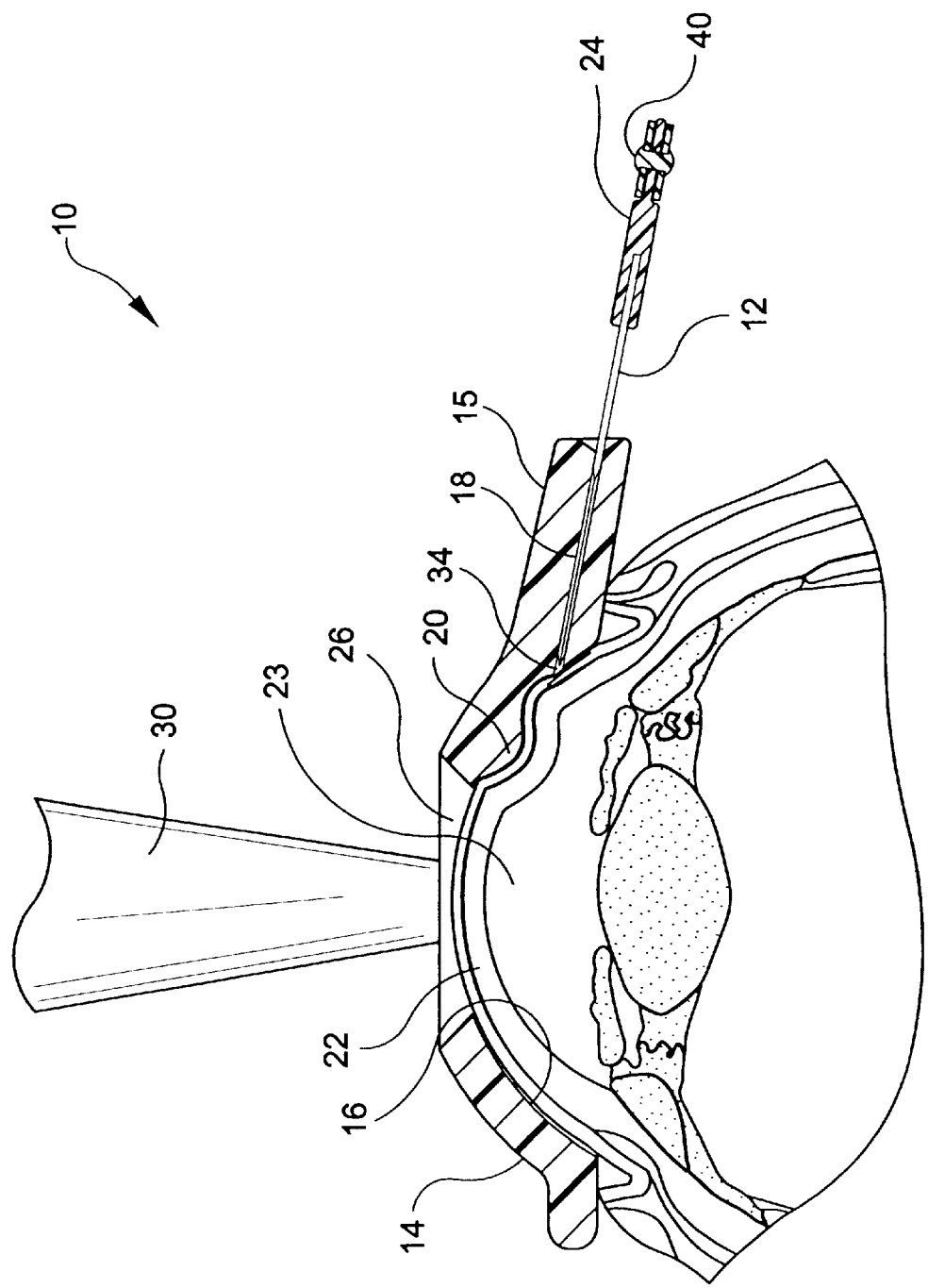
FIG. 6 is a schematic cross-sectional view of an alternate embodiment of the device of FIG. 1 analogous to FIG. 5.
Figure 7:
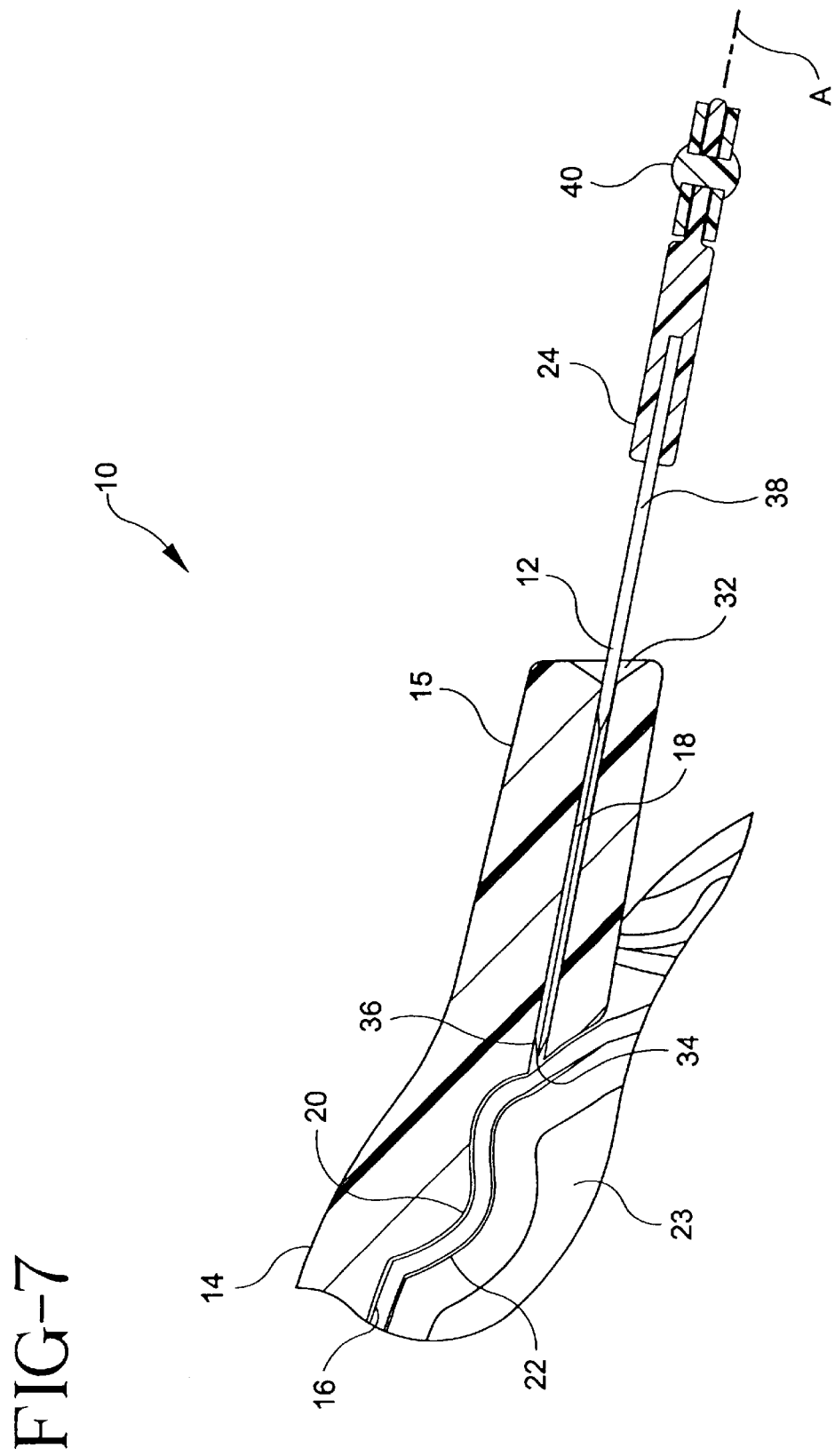
FIG. 7 is an enlarged cross-sectional detail of the device of FIG. 1 taken from FIG. 6.

In one embodiment, there is a protuberance 20, best seen in FIG. 6, affixed to inner surface 16 of the frame adjacent to aperture 18. Protuberance 20 is disposed to distort a surface 22 of a patient's eye 23 when device 10 is selectively positioned on eye 23 by a practitioner.

Blade 12 is attached to a cantilever 24 that is disposed on frame 14 to hold, advance and withdraw blade 12 through aperture 18. Preferably, cantilever 24 is either neutral in or biased to a rest position where blade 12 is in the position wherein blade 12 is contained within aperture 18. There is an opening 26 through frame 14 to inner surface 16. Opening 26 is disposed so that when a selectively applied vacuum source device is applied to frame 14 while device 10 is selectively placed on the eye of a patient by the practitioner, ambient air pressure retains device 10 in the selected position as long as the vacuum source is maintained. Other provisions for retention of frame 14 onto the patient's eye such as lateral ridges, a plurality of points, a plurality of bumps on inside surface 16 may be used either in combination with, or instead of, the vacuum source. Additionally, the bumps and ridges may be formed from a resilient material and applied to the inside surface. There is a grip, preferably finger grips as seen in FIGS. 1–6 in combination with or instead of a handle 30 affixed to frame 14 to facilitate the practitioner's manipulation of device 10. Aperture 18 of multi-plane corneal incision device 10 has a proximal opening 32, a longitudinal axis "A" and a distal opening 34 on inside surface 16 of frame 14.

In the embodiment where inside surface 16 includes protuberance 20, distal opening 34 is substantially coterminous with protuberance 20 so that when device 10 is selectively positioned on patient's eye 23 and blade 12 is advanced through distal opening 34, an incision is made through the surface into the anterior chamber of the eye in a region of the eye surface 22 conformed to protuberance 20.

One type of procedure that device 10 is suited for is referred to as a clear cornea procedure. For this procedure, blade 12 preferably is a keratome or slit blade. Blade 12 preferably has a spear shaped beveled sharp tip 36 as a cutting surface and sides 38 that are dull with respect to tip 36. Aperture 18 is sized, shaped and disposed so sharp tip cutting surface 36 can extend into the aperture a sufficient distance to cause the desired incision in the patient's eye when it is selectively advanced by the practitioner. A width "w" of aperture 18 should not be sufficient more than the width of blade 12 and a height "h" of the aperture should not be sufficiently greater than the thickness of blade 12 to allow movement of the blade substantially more than in one axis. The width clearance preferably is less than about 0.05 mm and the height clearance is preferably less than about 0.01. These clearances only allow the selective movement of the blade substantially in one axis with respect to frame 14. For other types of procedures, other blade shapes may be preferred and are considered within the scope of the disclosure.

The distortion of the patient's eye surface 22 by protuberance 20 when device 10 is selectively positioned on the patient's eye results in the incision made by advancement of blade 12 having a complicated multi-plane geometry. As described above, such an incision generally is able to close and hear without the need for sutures. The exact shape of protuberance 22 and the exact position of aperture 18 in relation to the protuberance is dependent on the desired geometry of the incision to be made. Generally, the desired shape of the incision is substantially "S" shaped. For applications where a planar incision is desired, a tangent line angle a best seen in FIG. 5, where the incision contacts the outer surface of the cornea is about twelve degrees to about twenty degrees and preferably an incidence angle of about seventeen and one half degrees is selected for the axis "A" of the aperture to interior surface 16 of frame 14. For other procedures and types of incisions other incidence angles may be preferred and are considered within the scope of this disclosure.

Figure 5:
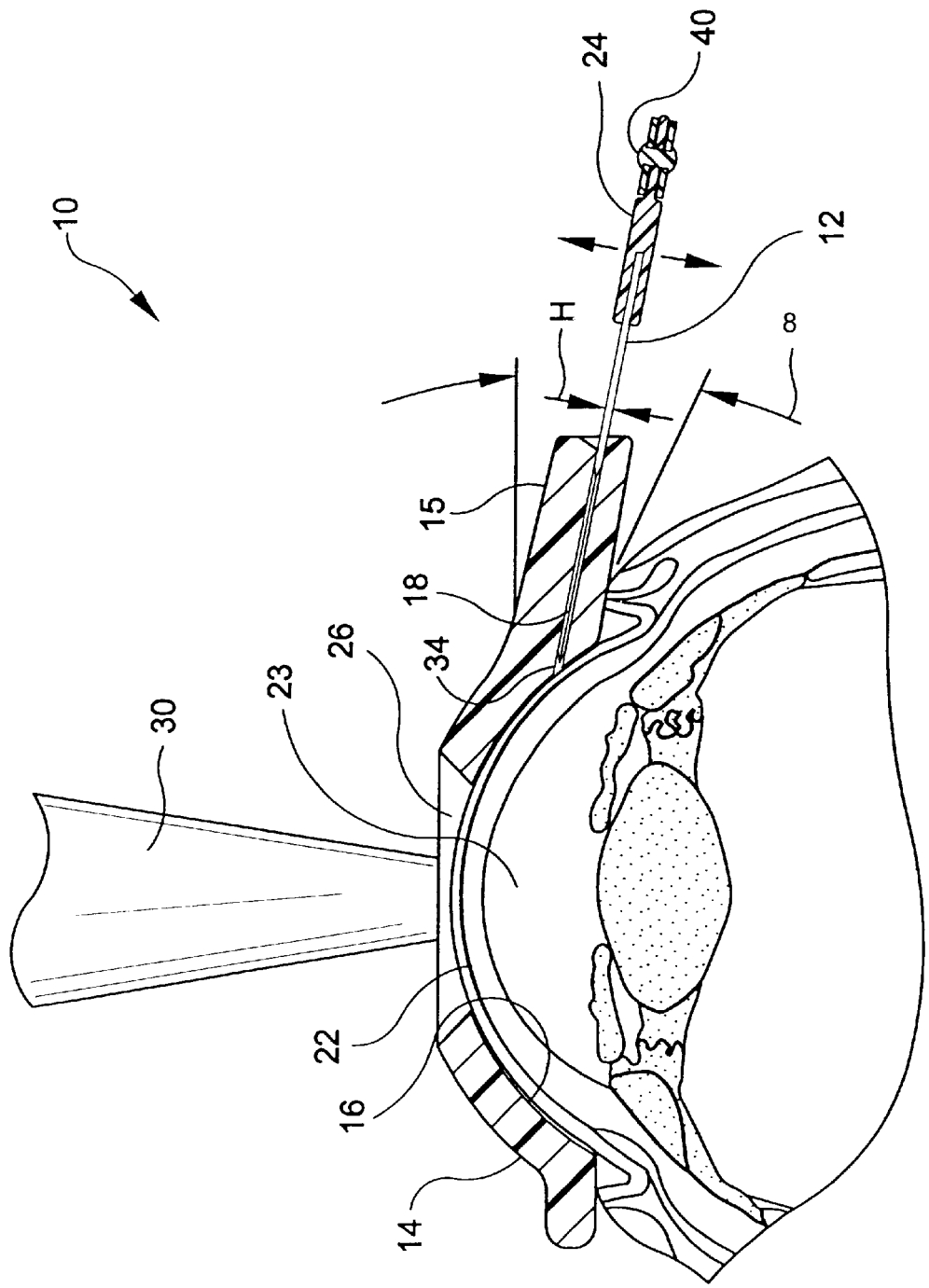
FIG. 5 is a schematic cross-sectional view of the device of FIG. 1 taken along the line 5—5 as mounted on the eye of a patient.

Referring to FIGS. 1–7, cantilever 24 is disposed from a pivot position 35 on a first side of frame 14, preferably about diametrically opposite aperture 18, to attach to blade 12 at a second pivot, preferably a ball and socket 40, disposed to facilitate movement of blade 12 through aperture 18. Other types of pivots may be envisioned, and are considered within the scope of this disclosure. Preferably, cantilever 24 includes a selectively releasable latch 42 with a finger release 44, so that if a practitioner holds device 10 between the thumb and middle finger, using grips 46 and 47, respectively, the practitioner's index finger is positioned on finger release 44. In use, the practitioner would selectively position device 10 on patient's eye as schematically illustrated in FIG. 5, using finger grips 46 and 47 in conjunction with handle 30. When the desired positioning is obtained, the practitioner would use the index finger to apply sufficient pressure on finger release 44 to release latch 42 and apply sufficient squeezing pressure to cantilever 24 to move blade 12 from aperture 18 to project beyond inner surface 16 and form the desired incision through patient's eye surface 22. After forming the incision, the practitioner releases the pressure on grips 46 and 47 thus allowing cantilever 24 to return blade 12 to the rest position within aperture 18.

Suitable materials for forming frame 14 include, but are not limited to metallic materials such as stainless steel, titanium and the like, polymeric materials such as polycarbonate, polysulfone, acrylonitrilelbutadiene/styrene (ABS), and the like. Scalpel blade 12 may be formed from stainless steel, polymeric materials such as polycarbonate, acrylics and the like, or ceramics such as zirconia, diamond, silicon and titanates. Cantilever 24 may be integrally formed with frame 24 or formed separately and assembled. When materials are selected for forming components of device 10, compatibility with various sterilization procedures must be considered.

FIGS. 7, 8, 9, 10, 11 and 12 illustrate other embodiments of the multi-plane corneal incision device of the invention. In these embodiments, alternates to cantilever 24 are disposed on frame 14 at projection 15 to hold, advance and withdraw blade 12 through aperture 18. Accordingly, substantially similar components that perform substantially similar functions are numbered identically to those components of the embodiments of FIGS. 1–6 except that a hundreds digit is used to identify those components of FIGS. 7–12. Additional equivalent embodiments to hold, advance and withdraw blade 12 through aperture 18 may be envisioned by one skilled in the art after study of this disclosure. These equivalents are considered within the scope of the disclosure.

Figure 8:
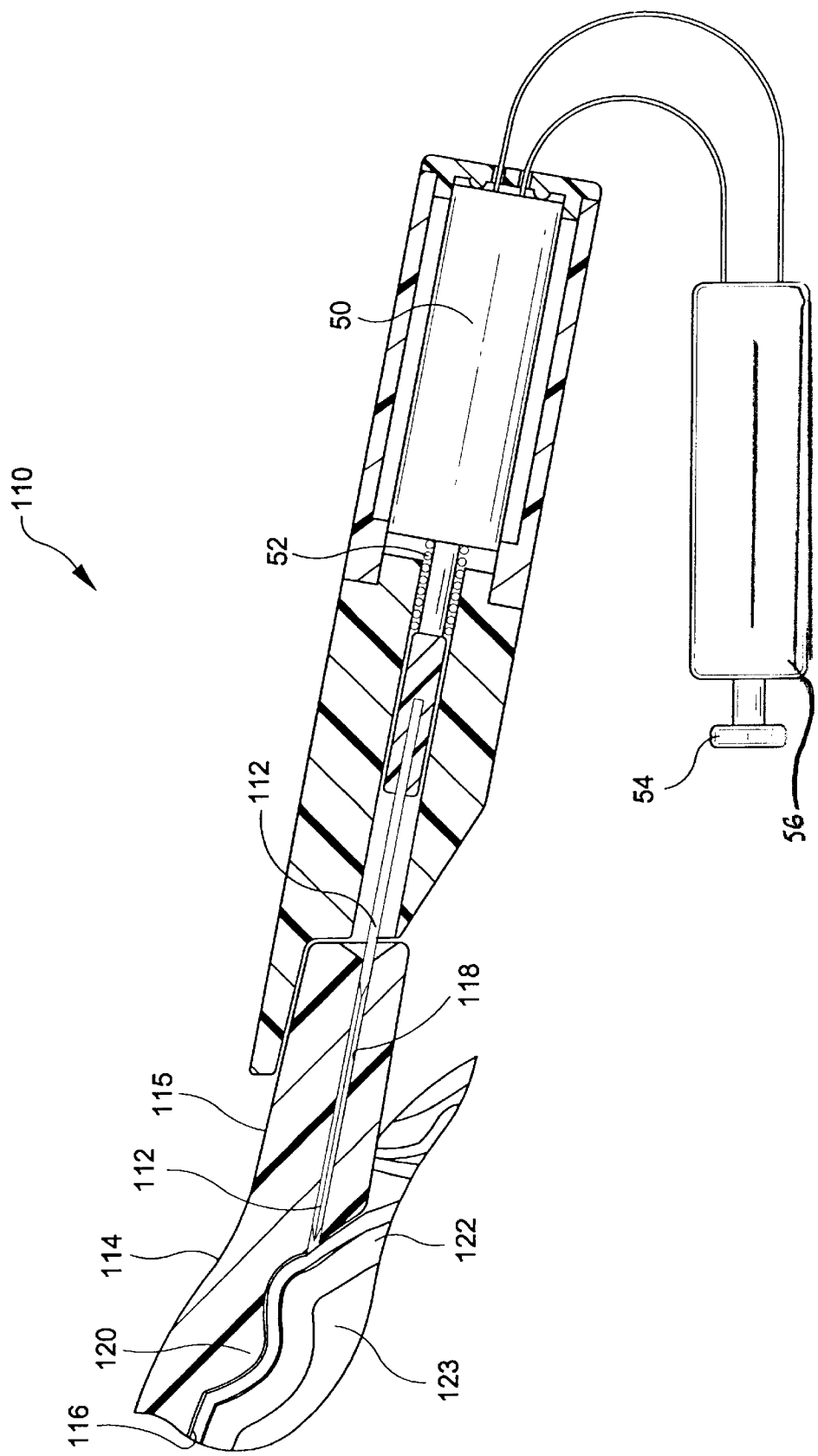
FIG. 8 is an enlarged cross-sectional detail analogous to FIG. 7 with an alternate blade movement system.

Referring to FIG. 8, projecting portion 115 from frame 114 of device 110 is illustrated. In this embodiment, an electrical solenoid 50 with a bias spring 52 is activated by a switch 54 on a power source 56. When solenoid 50 is not activated, bias spring 52 keeps blade 112 within aperture 118. When solenoid 50 is activated by the practitioner, blade 112 is urged to project beyond inner surface 116 of frame 114 and form the desired incision through surface 122 into the anterior chamber of patient eye 123.

Figure 9:
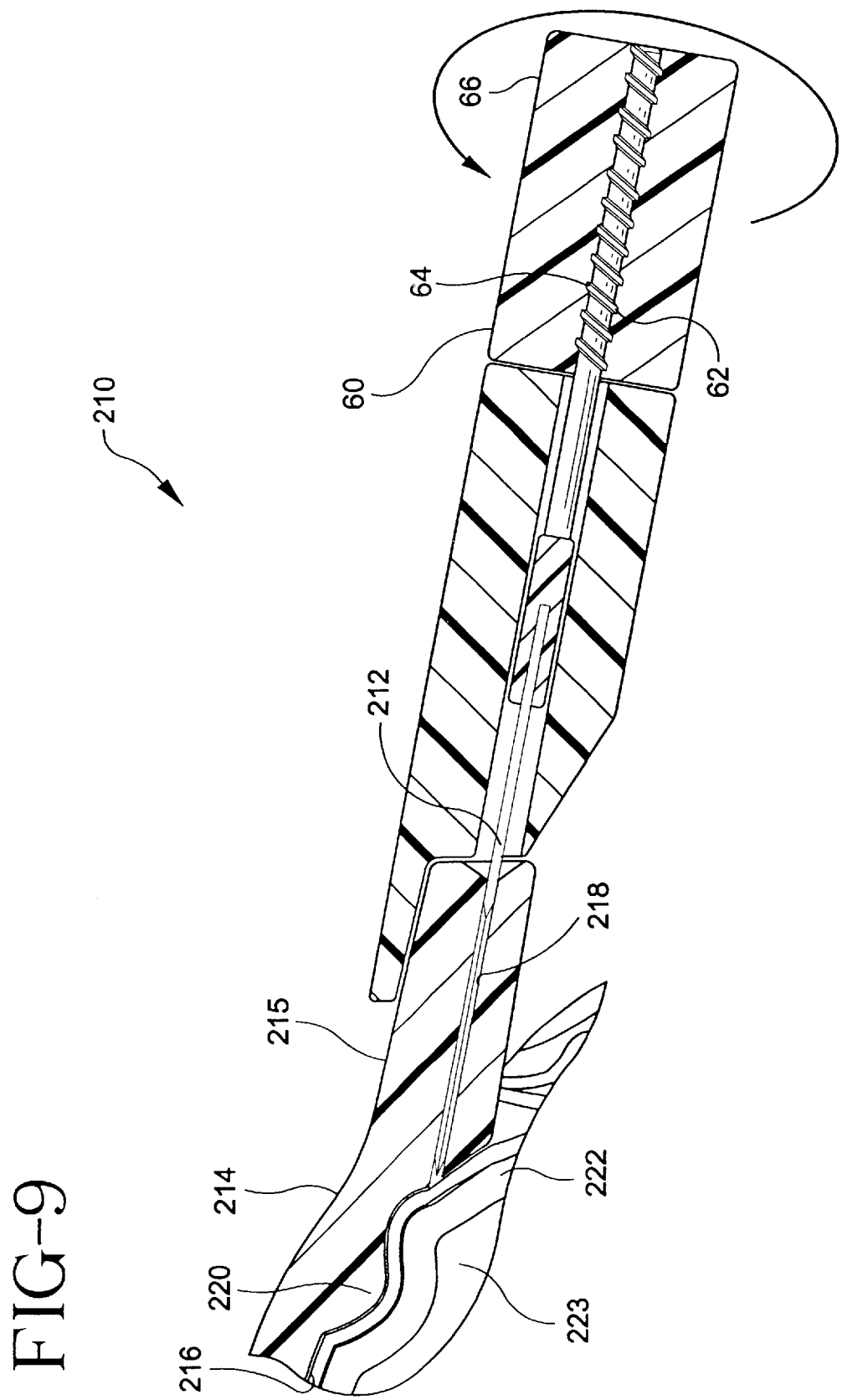
FIG. 9 is analogous to the view of FIG. 7 with another blade movement system.

Referring to FIG. 9, projecting portion 215 from frame 214 of device 210 is illustrated. In this embodiment a mechanical threaded advance and retraction mechanism 60 is mounted on projecting portion 215. The practitioner turns a knob 66 in a first direction so that conjugate threads 62 and 64 selectively advance blade 212 through aperture 218. When blade 212 is advanced beyond inner surface 216 of frame 214 a sufficient distance, desired incision is formed through surface 222 into the anterior chamber of patient eye 223. Blade 212 is selectively withdrawn back into aperture 218 by turning knob in the reverse direction to return blade 212 to the origination position.

Figure 10:
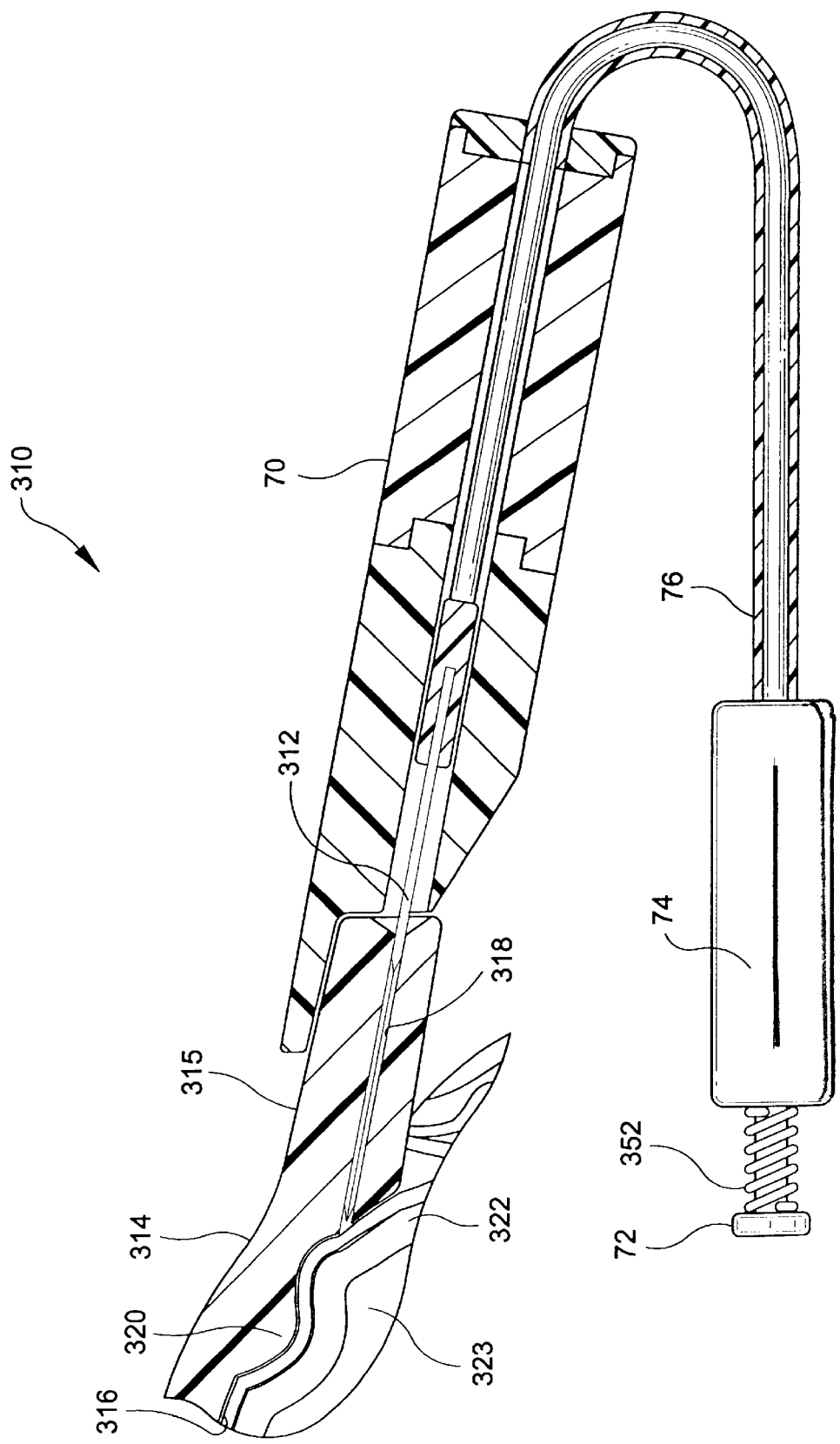
FIG. 10 is analogous to the view of FIG. 7 with yet another blade movement system.

Referring to FIG. 10, projecting portion 315 from frame 314 of device 310 is illustrated. Projecting portion 315 includes a mechanical cable control mechanism 70 with a button release 72 mounted on a finger support 74 that is attached to a cover connecting cable 76. Finger support 74 includes a bias spring 352 that is overcome by the practitioner's finger pressure sufficient to advance blade 312 to project beyond inner surface 316 to form the desired incision through surface 322 into the anterior chamber of patient eye 323. When the practitioner releases the pressure from button release 72, spring 352 returns blade 312 to the original position within aperture 318.

Figure 11:
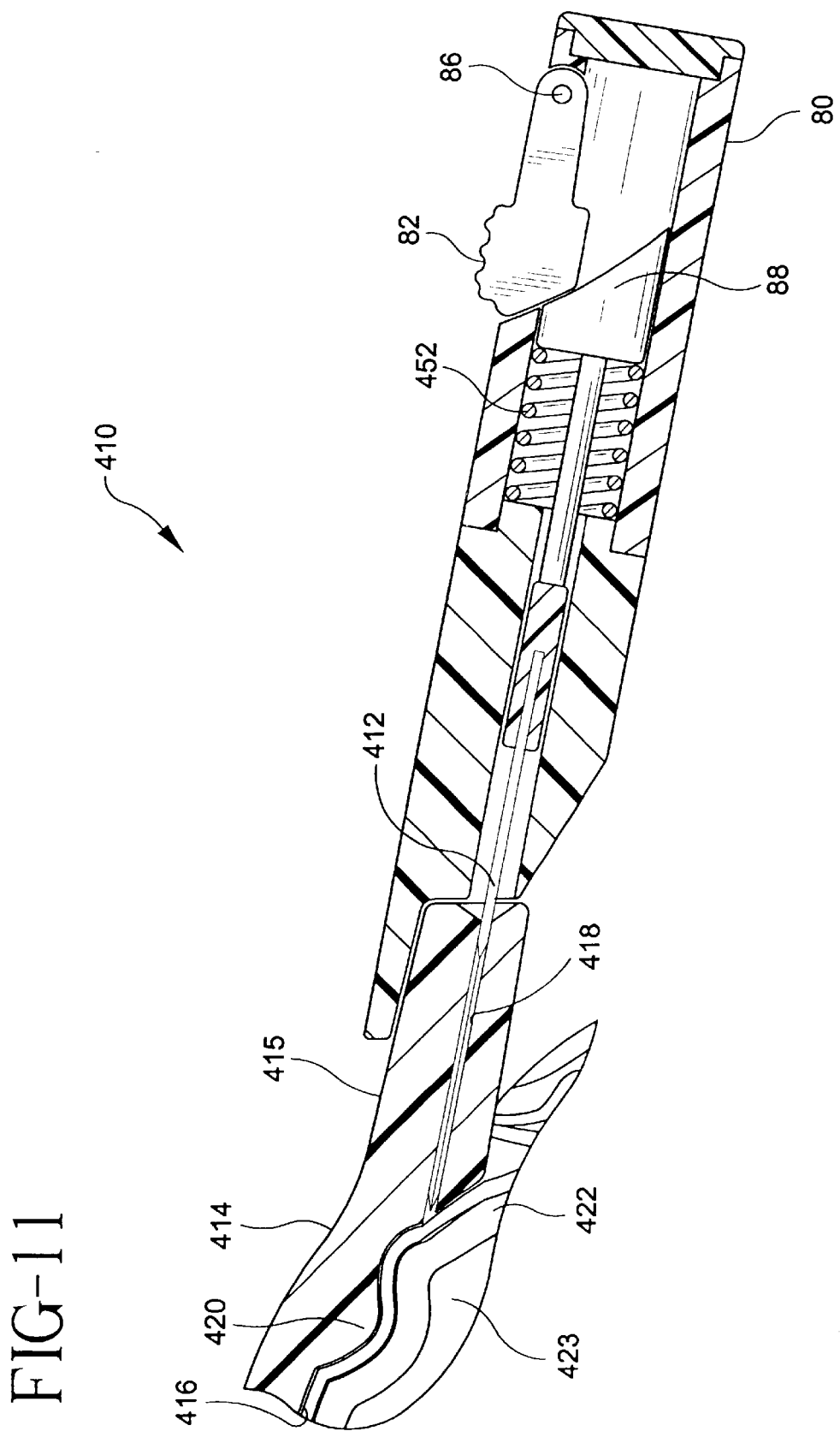
FIG. 11 is analogous to the view of FIG. 7 with a further blade movement system.

Referring to FIG. 11, projecting portion 415 from frame 414 of device 410 is illustrated. Projecting portion 415 includes a mechanical cam/cam follower mechanism 80 for advancing and retracting blade 412. When a practitioner applies sufficient finger pressure to cam 82, to overcome a bias spring 452, cam 82 pivots at pivot point 86 and cam follower 88 is urged distally to advance blade 412 a sufficient distance through aperture 418 to project beyond inner surface 416 of frame 414 to form the desired incision through surface 422 into the anterior chamber of patient eye 423. As the pressure is released from cam 82, bias spring 452 returns blade 412 to the original position where it no longer projects beyond inner surface 416.

Figure 12:
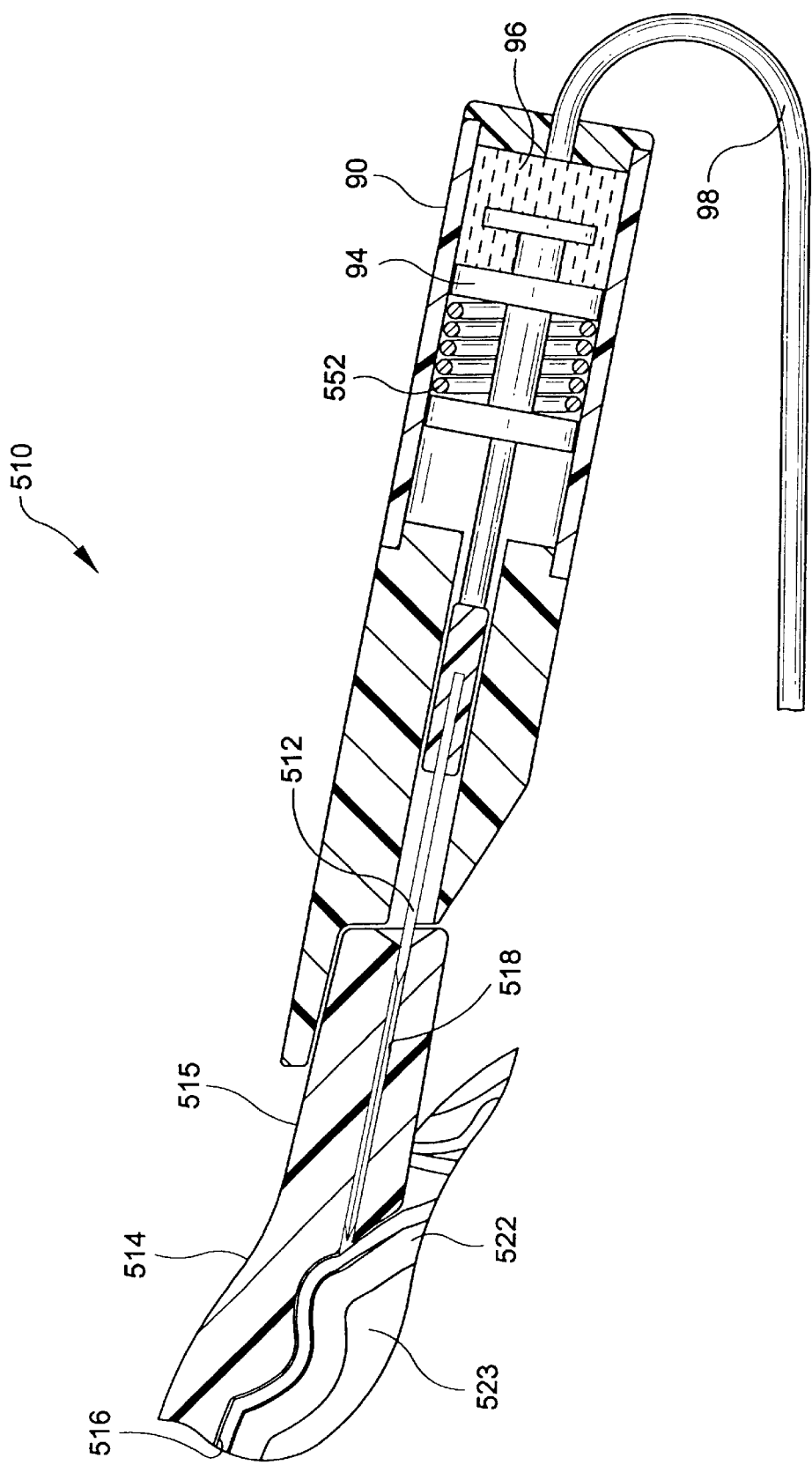
FIG. 12 is analogous to the view of FIG. 7 with an additional blade movement system.

Referring to FIG. 12, projecting portion 515 from frame 514 of device 510 is illustrated. Projecting portion 515 includes a hydraulic actuated mechanism 90 such as advancing a piston 94 against a bias spring 552 to urge blade 512 through aperture 518 to project beyond inner surface 516 and form the desired incision through patient eye surface 522 into the anterior chamber of the patient's eye. Other hydraulically actuation mechanisms such as an elastomeric diaphragm may be envisioned and are considered within the scope of this disclosure. The hydraulic pressure sufficient to overcome bias spring 552 is supplied from a source 98. When the hydraulic pressure is released, bias spring 552 returns blade 512 to the original position within aperture 518.

The corneal incision device of the invention combines a placement and location device with the sharp surgical blade and the activation mechanism. This combination allows the practitioner to selectively place the location device on the patient's eye in the desired position, and once the desired placement is achieved, activate the surgical blade to make the complex incision without having to pick up another instrument. Thus, the correct placement of the device by the practitioner substantially ensures that the desired complex incision is formed and the rest of the procedure can then proceed.

Figure 13:
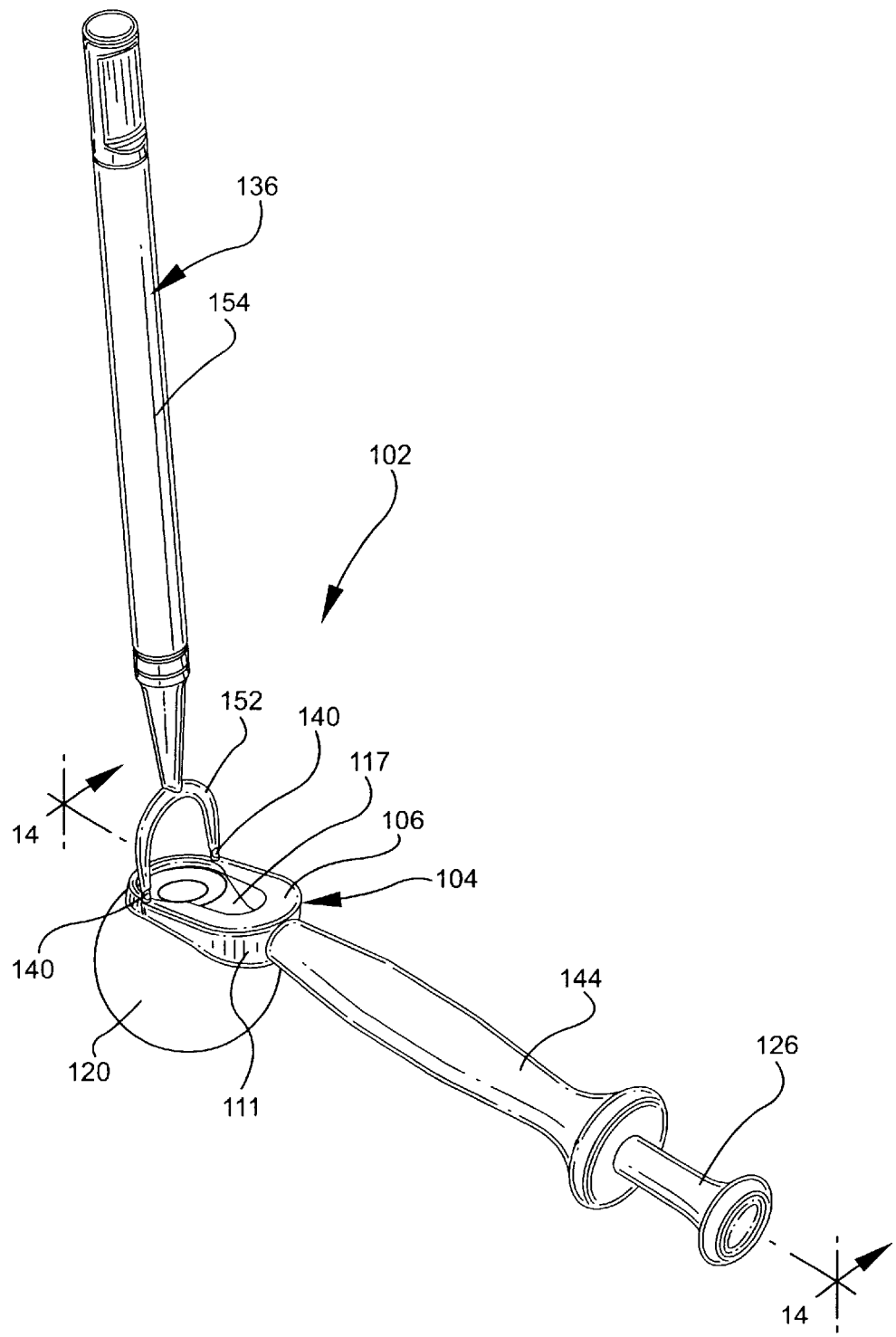
FIG. 13 is a perspective view of another preferred embodiment of a corneal incision device of the present invention.

A corneal incision device in accordance with the subject invention is identified generally by the numeral 102 in FIGS. 13–26. Device 102 includes a frame 104 having a top 106, a bottom 108 and a side 111. The frame defines an aperture 113 therein. The frame also defines a hole 117 to access an eye 120 as shown in FIG. 13. As shown in FIG. 15, top 106 defines a plane "B". The device further includes a blade 121 supported by the frame. The blade is at a fixed angle "Δ". The fixed angle is relative to the frame with regards to plane "B". The device further includes an actuator 126 attached to the blade for advancing and withdrawing the blade at the fixed angle through the aperture of the frame. The advancement of the blade creates an incision 130 on the eye at fixed angle Δ.

Figure 18:
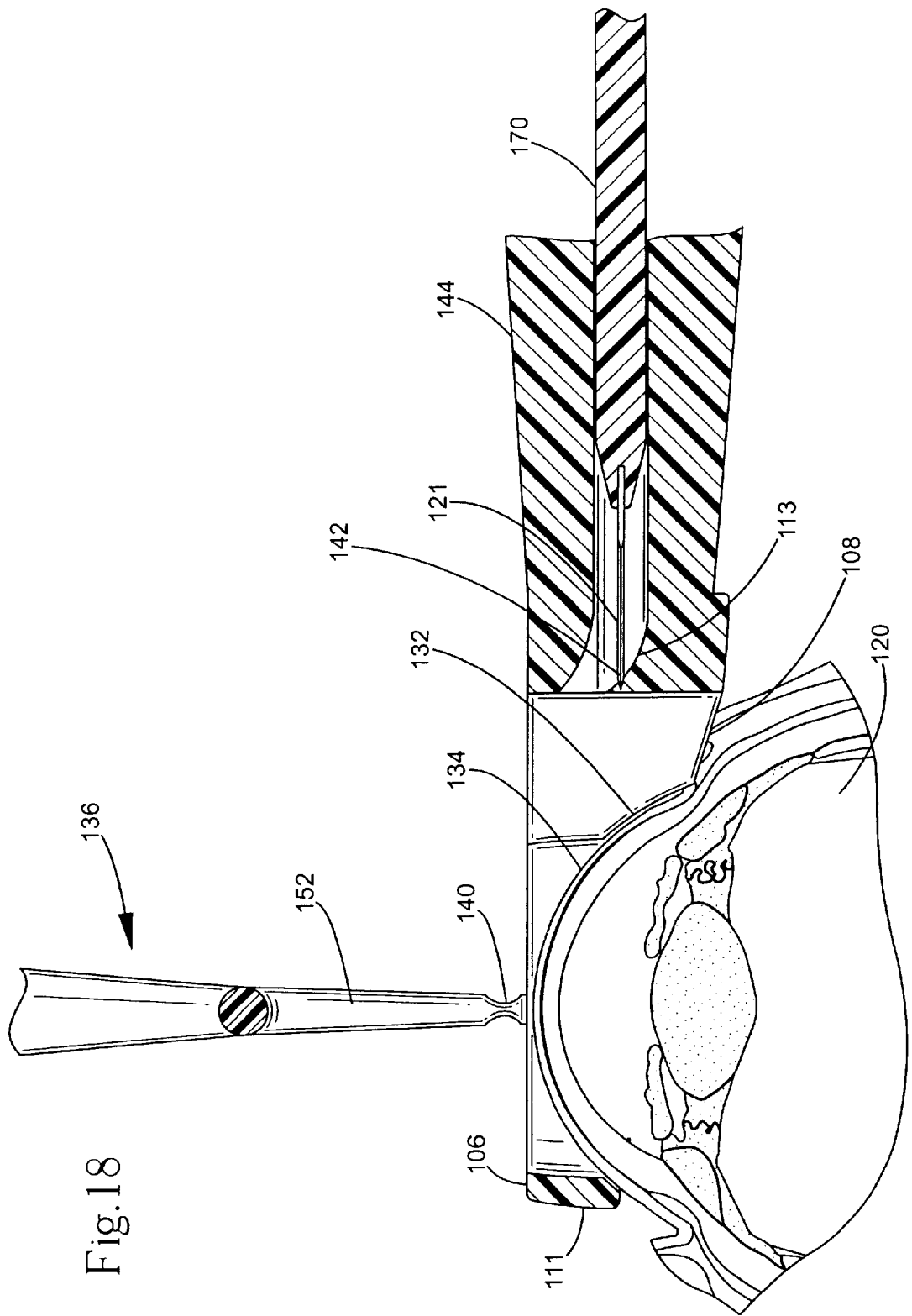
FIG. 18 is an enlarged cross-sectional view of FIG. 17 taken along line 18—18.

Adverting to the drawings, FIG. 13 illustrates a preferred embodiment of device 102. Preferably, the bottom of the frame includes a surface 132 on bottom 108. The surface is contoured to the curvature of the eye and dimensioned to provide the fixed angle to the blade relative to the frame. This fixed angle and contoured bottom is illustrated in the sectional view in FIGS. 14–16. Alternatively, the aperture can be formed arcuate to create the fixed angle for the blade to follow when it is being advanced and withdrawn. An arcuate aperture 142 is illustrated in FIG. 18. There are many other methods of creating the fixed angle for the blade which are all within the scope of the present invention. Such methods would include for example, making the blade arcuate, making any blade connectors or mechanisms to move the blade arcuate, and combinations thereof. The advantage of the present invention is that the blade is at a fixed angle so that the practitioner does not have to estimate and fix the blade at the correct incision angle. Additionally, it is within the scope of the present invention to provide several different corneal incision device containing a wide variety of fixed incision angles. The change in the fixed incision angle and thus the fixed angle of the blade is made by altering the angle in the surface on the bottom of the frame. Alternatively, by altering the fixed blade angle by any of the several methods described above would enable the device to accommodate any angle of incision.

Figure 20:
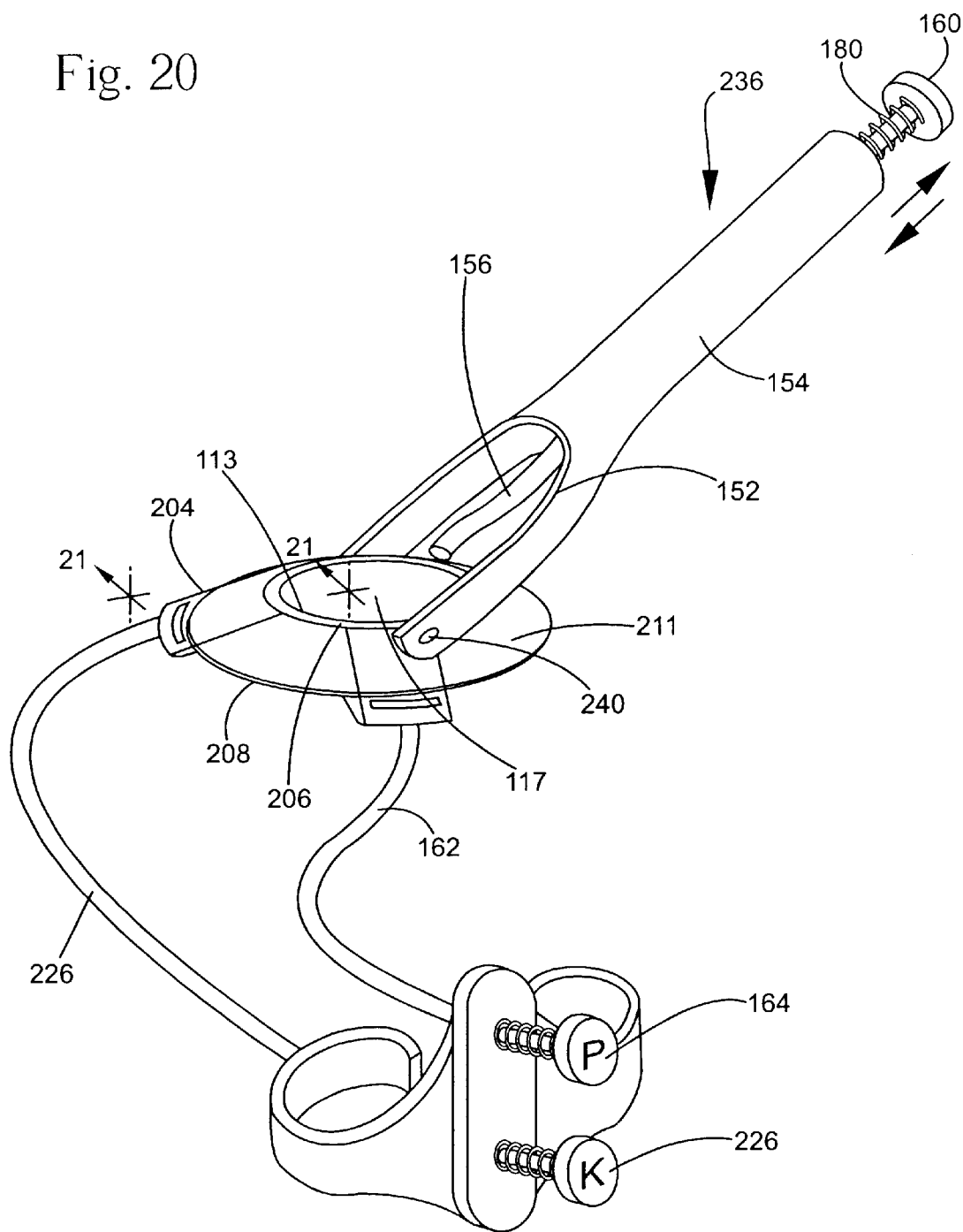
FIG. 20 is a perspective view of an alternate embodiment of FIG. 13.

Device 102 may further include at least one handle 136 to hold the frame on the eye. As shown in FIG. 13, handle 136 further includes a stem 154 and a fork portion 152. The fork portion further includes at least one pivot point 140. The pivot point as illustrated in FIG. 13 is attached to the top of the frame, however, the pivot point may also be attached to the side of the frame as shown in FIG. 20. The pivot point allows the practitioner to rotate the handle relative to the frame to provide clearance to hole 117, thereby giving access to the eye.

Device 102 may further include a housing 144. Housing 144 is fixedly attached to the side of the frame for protecting the blade therein. An actuator 126 is attached to the blade to advance and withdraw the blade through the aperture of the frame. Preferably, the blade is attached to a blade cartridge 170. However, it is within the scope of the invention for the blade to be directly attached to the actuator.

As shown in FIGS. 13–16, actuator 126 is preferably a plunger. However, it is within the scope of the invention that actuator 126 can be a manually activated cantilever arm, mechanical release including a bias spring, an electrical solenoid, a hydraulically activated mechanism, a pneumatically actuated mechanism, a vacuum actuated mechanism, a cam cam follower, a cable release against a mechanical biasing spring, a plunger against a biasing spring or combinations thereof. Actuator 126 is allowed to move distally and proximally to advance and withdraw, respectively, the blade inside the housing. The surface on the bottom of the frame allows the blade to incise the eye at the fixed angle. This embodiment is preferred since the practitioner does not have to adjust the blade to obtain the angle desired for the incision made by the blade.

Figure 14:
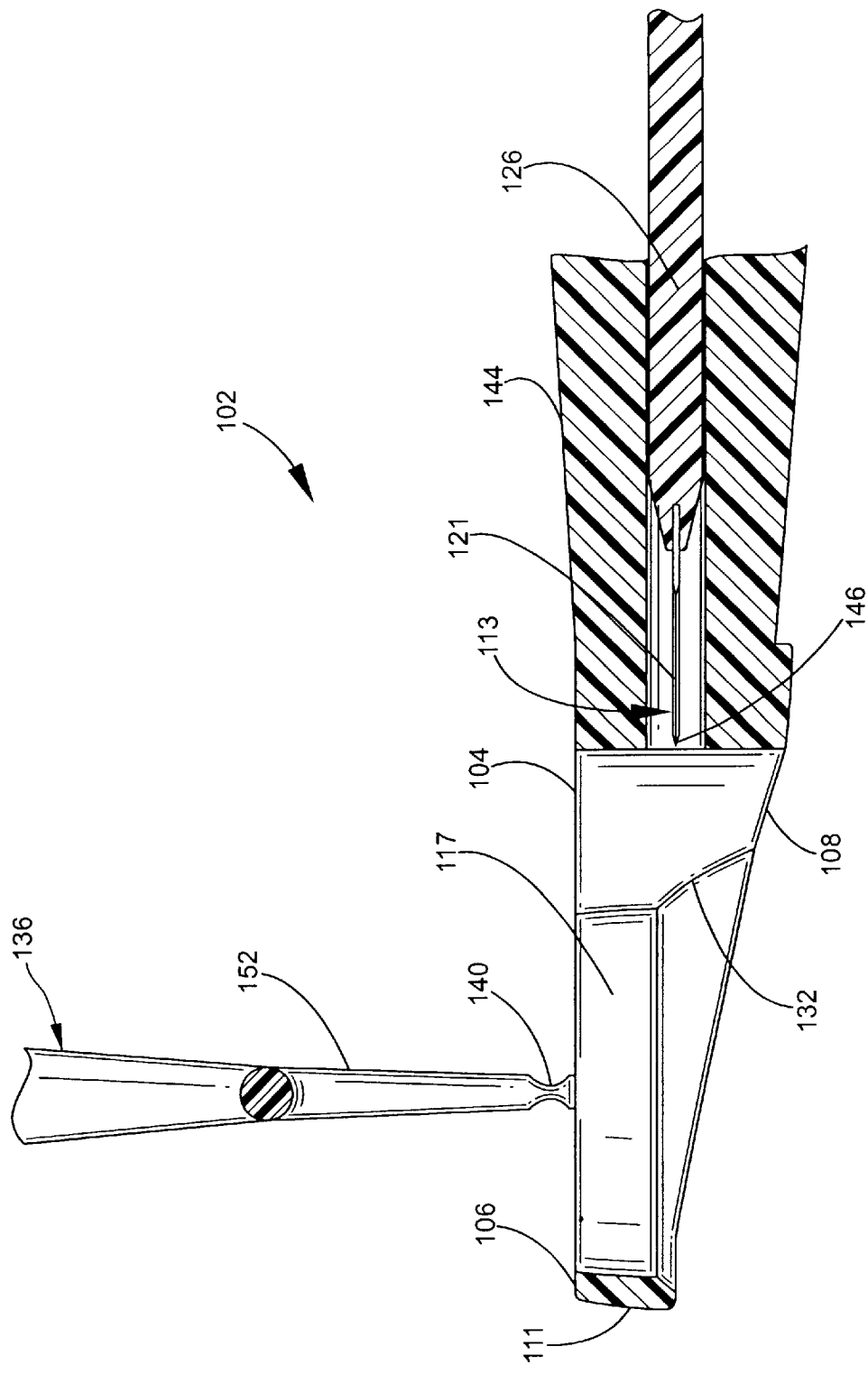
FIG. 14 is an enlarged cross-sectional view taken along line 14—14 in FIG. 13.
Figure 15:
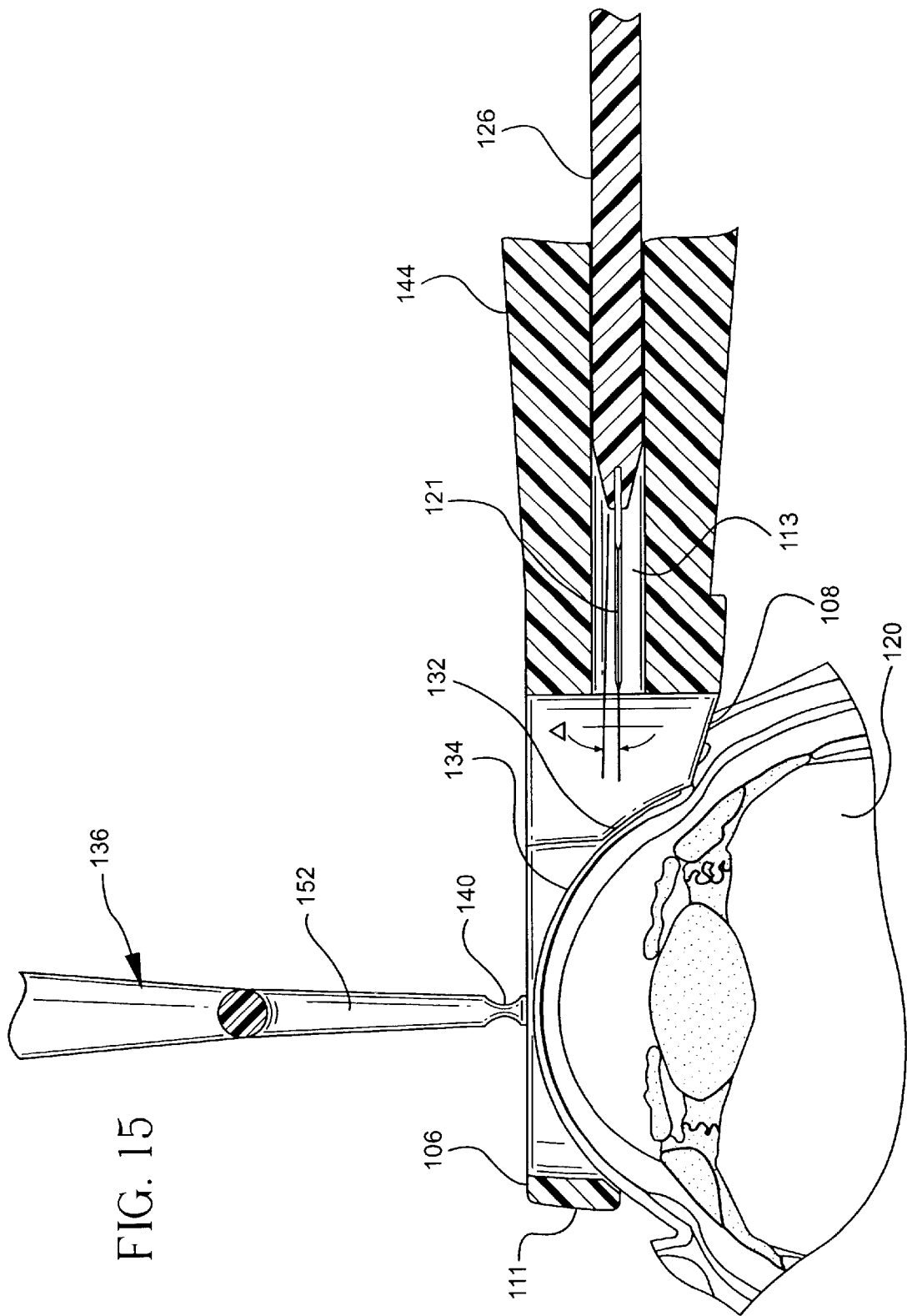
FIG. 15 is an enlarged cross-sectional view of FIG. 14 with the device in FIG. 14 applied to the eye.

FIG. 14 shows a curvature 132 of the eye and how surface 132 of the bottom of the frame is contoured to match the curvature. Preferably, it is the bottom of the frame that gives the blade its fixed angle relative to plane "B" of the frame. However, as previously stated, the aperture can be made arcuate to also provide the fixed angle of the blade.

Figure 16:
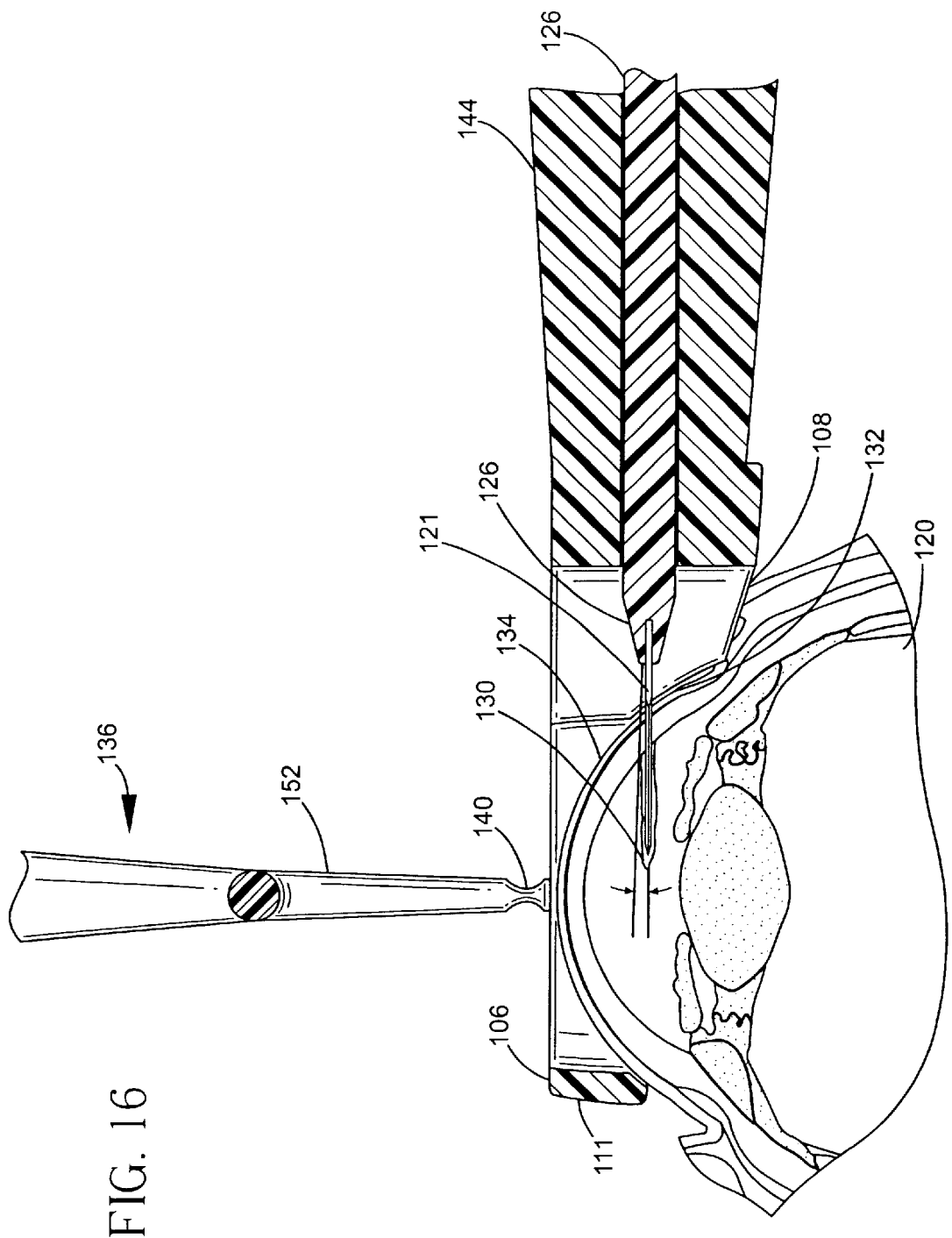
FIG. 16 is the cross-sectional view of FIG. 15 with the blade extended into the eye.

FIG. 16 illustrates blade 121 advancing and making incision 130. The blade is advanced and withdrawn at fixed angle $\Delta$ to create the incision at fixed angle $\Delta$.

Figure 19:
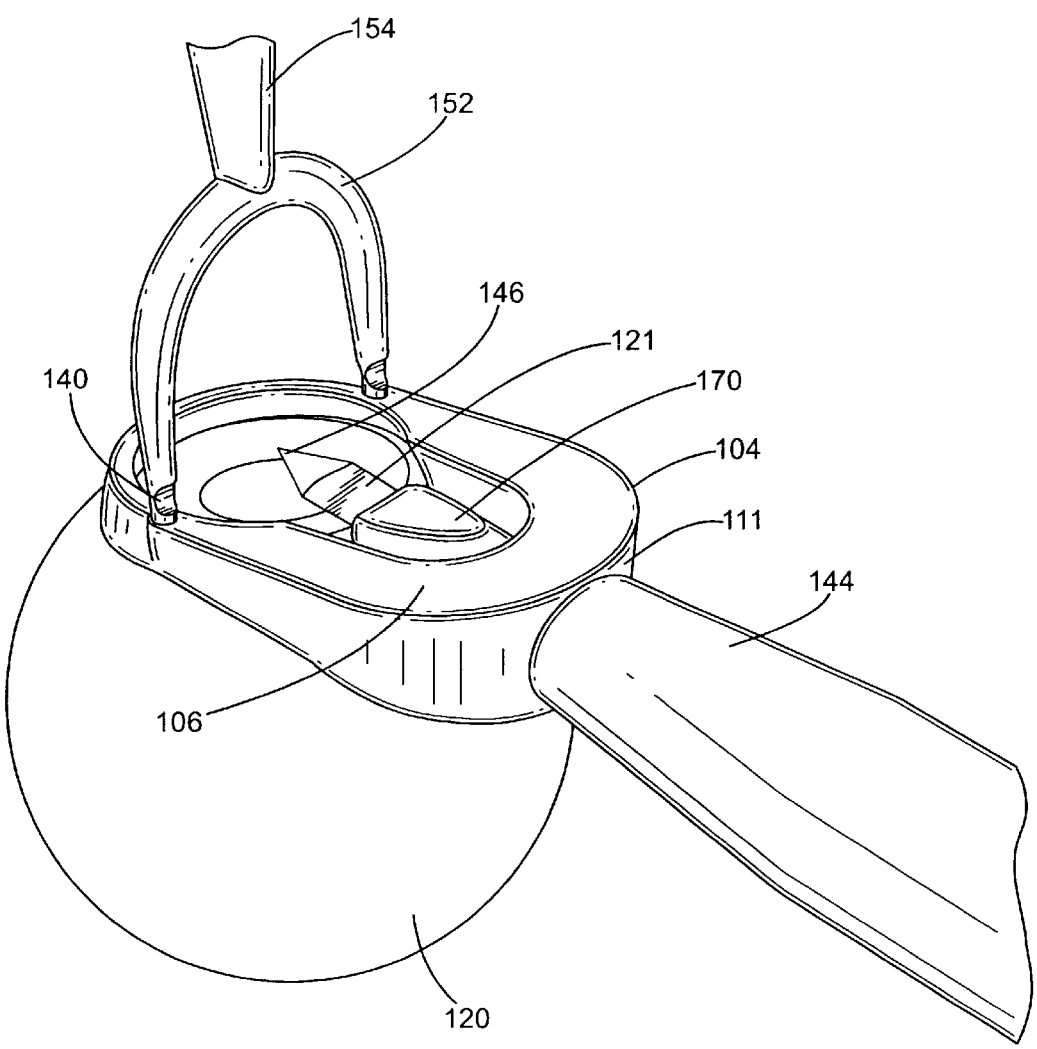
FIG. 19 is an enlarged perspective view of FIG. 17 with the blade extended.

FIG. 19 illustrates blade 121 further including a distal tip 146. Preferably, the distal tip is a beveled spear-shaped sharp tip. However, it is within the scope of this invention to include any blade geometry. Such geometries include diamond shaped, round cut, hooked shaped, and multi-beveled shaped. Blade 121 is attached to blade cartridge 170 as shown in FIG. 19. Preferably, blade cartridge 170 is attached to blade 121. However, it is within the scope of this invention that the actuator can be directly connected to the blade as shown in FIGS. 14 and 15.

An alternative embodiment to corneal incision device 102 is shown in FIG. 20. In this alternate embodiment, a corneal incision device 202 also includes a frame 204, a top 206 and a bottom 208. Frame 204 also includes a side 211. In this alternate embodiment a handle 236 is attached to the frame on side 111. Handle 236 has at least one pivoting point 240. Pivoting point 240 allows the handle to pivot about the frame. Preferably, pivoting point 240 is mounted on side 211. However, pivoting point 240 can also be mounted on top 206. The handle is used to hold device 202 in place on the eye. The pivot motion allows the practitioner to move the handle to allow access to the eye through hole 117.

Frame 204 also has bottom 208 contoured to the curvature of the eye as in the preferred embodiment to provide the fixed angle of the blade. This configuration is shown in the cross sectional view in FIG. 21. It is within the scope of the present invention to include the previously mentioned methods of creating a fixed blade angle as in device 102. For example, the aperture of frame 204 can also be arcuate as in the preferred embodiment so that the blade is positioned at a fixed angle relative to the frame.

The blade is advanced and withdrawn by an actuator 226. Again, as with the preferred embodiment, the actuator is preferably a plunger. However, like the preferred embodiment other means for actuating the blade can be used which were previously listed. These means include a bias spring, an electrical solenoid, a hydraulically activated mechanism, a pneumatically activated mechanism, a vacuum actuated mechanism, a cam and cam follower, a cable release against a mechanical biasing spring, a plunger against a biasing spring or combinations thereof.

The handle attached to frame 204 further includes a vacuum source 156. Vacuum force 156 assists the practitioner in holding frame 204 in a selected position against the eye. A switch 160 is mounted on the handle to activate the vacuum source. Switch 160 can move distally and proximally in relationship to the handle to activate the vacuum source. It is within the scope of the invention to include switch configuration know to those skilled in the art. Such configurations include slide switches, push buttons, knobs, membrane switches, and rotating switches. Vacuum source 160 is connected to frame 204. A secondary vacuum source 162 may also be attached to frame 204 as shown in FIG. 20. The second vacuum source is controlled by at least one control button 164 which is located adjacent to actuator 226 that provides advancement and withdrawal of the blade.

Figure 22:
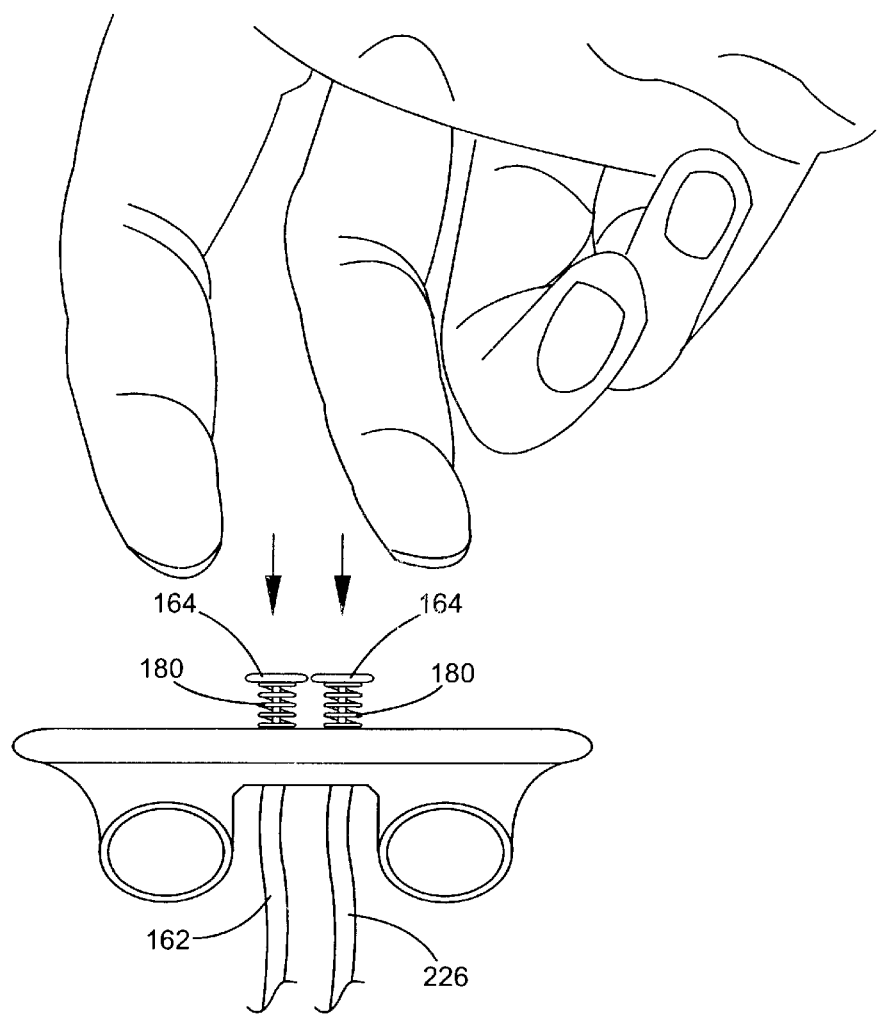
FIG. 22 is an enlarged view of FIG. 20 illustrating activation.

FIG. 22 illustrates activation of control button 164 and actuator 226 so that frame 204 can be selectively held in place on the eye while the blade is being advanced and withdrawn.

Figure 23:
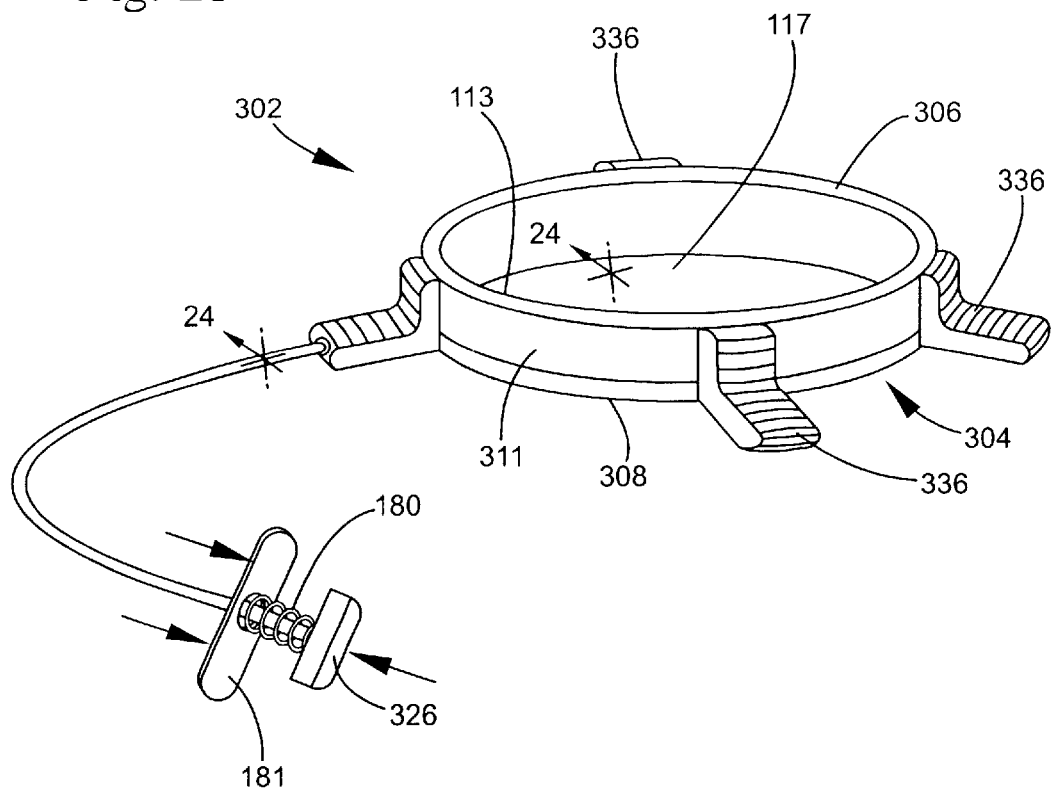
FIG. 23 is a perspective view of an alternate embodiment of the invention in FIG. 13.

Adverting to FIG. 23, shown is another alternate embodiment of corneal incision device 102. Shown in FIG. 23 is a corneal incision device 302. Device 302 includes a top 306, a bottom 308, and a side 311. Frame 304 further defines an aperture 113 and a hole 117. Similar to device 102 and device 202, aperture 113 is for the blade to travel through the frame and hole 117 is for access to the eye. Preferably, bottom 311 is contoured to the curvature of the eye similar to the preferred corneal incision device 102 for providing the blade with fixed angel Δ. This allows the blade to be at the fixed angle relative to the frame so that when the blade is advanced and withdrawn, the blade incises the eye at the fixed angle through the aperture of the frame. Frame 304 further includes at least one handle 336. Handle 336 is preferably disposed on side 311. However, handle 336 can be also mounted on top 306. Again, the function of handle 336 is to hold the frame in place in a selected position on the eye. Device 302 further includes an actuator 326. Actuator 326 is preferably a plunger, however, it is within the scope of the invention for device 302 to also incorporate the actuating means previously listed for device 102 and device 202.

Figure 24:
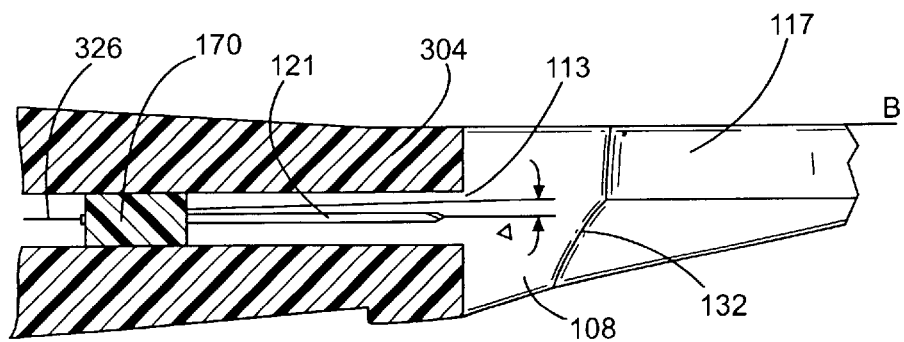
FIG. 24 is a cross-sectional view taken along line 24—24 in FIG. 23.

FIG. 24 illustrates a cross-sectional view taken along line 24—24 of FIG. 23. In particular, FIG. 24 shows a cross-sectional view of actuator 326. In this embodiment, blade 121 is held by blade cartridge 170. However, it is within the scope of the invention that blade 121 can be directly connected to actuator 326. Actuator 326 further includes a biasing spring 180 and a flange 181. Biasing spring 180 is used to return the actuator to its original position after it has been depressed. Upon depressing actuator 326 blade 121 moves distally through aperture 113. When the actuator 326 is released, biasing spring 180 is forced to move actuator 326 and blade 121 proximally back inside frame 304 by the resistance the spring encounters from the flange. Alternatively, the spring can be eliminated from this embodiment and actuator 326 can be manually moved to provide advancement and withdrawal of the blade.

Figure 25:
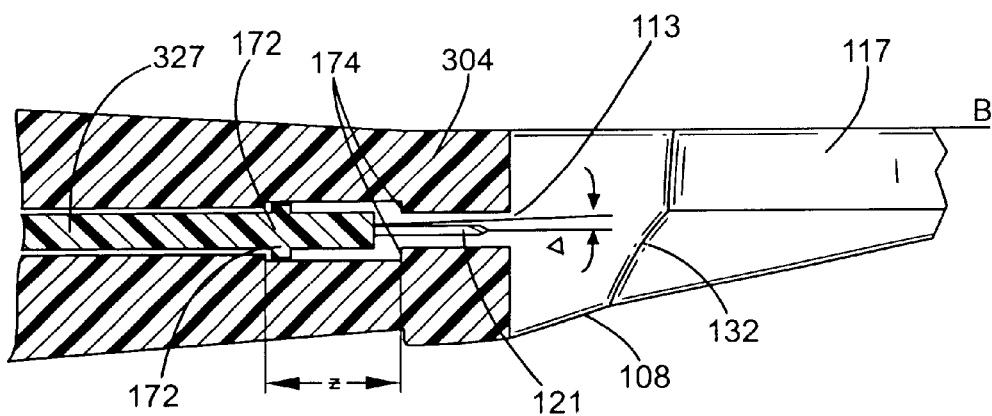
FIG. 25 is an alternate embodiment of the cross sectional view in FIG. 24.
Figure 26:
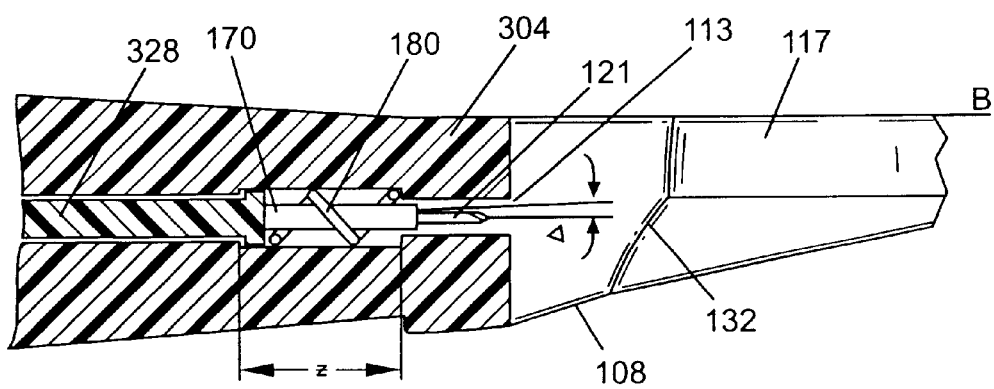
FIG. 26 is another alternate embodiment of the cross sectional view in FIG. 24.

FIGS. 25–26 are alternate embodiments of actuator 326. Shown in FIG. 25 is an actuator 327. Actuator 327 uses an pneumatically actuated mechanism to move blade 121 forward. Actuator 327 further includes at least one wing 172 which defines an incision length "Z". Length "Z" is defined as the distance that wing 172 travels to meet with an inner wall 174 of frame 304. Air moves actuator 327 and blade 121 distally. Distal motion is limited by wing 172 contacting inner wall 174. Upon proximal air flow, actuator 327 moves proximally forcing blade 121 back inside aperture 113.

Adverting to FIG. 26, shown is another alternate actuator 328. Actuator 328 incorporates bias spring 180 to determine incision length "Z". Blade 121 is held by blade cartridge 170. However, it is within the scope of the invention that blade 121 could be attached directly to actuator 328. Upon distal motion of actuator 328, spring 180 is compressed forcing blade 121 through aperture 113 to incise the eye. When force is released from actuator 328, bias spring 180 forces actuator 328 and cartridge 170 and blade 121 in a proximal motion. This proximal motion forces blade 121 back through aperture 113 and withdraws the blade into frame 304.

The function of device 102 is relatively straightforward. Device 102 is held and placed on the eye. Frame 104 is secured on the eye by applying pressure to handle 136. Handle 136 can be rotated to allow access of the eye through hole 117. The blade is advanced to create an incision by applying distal motion to actuator 126. Upon distal motion of actuator 126, the blade travels through the aperture of the frame to incise the eye at a fixed angle. By applying proximal motion to actuator 126 the blade is withdrawn from the eye and back into housing 144. This mode of operation is seen in FIGS. 13–19.

Figure 17:
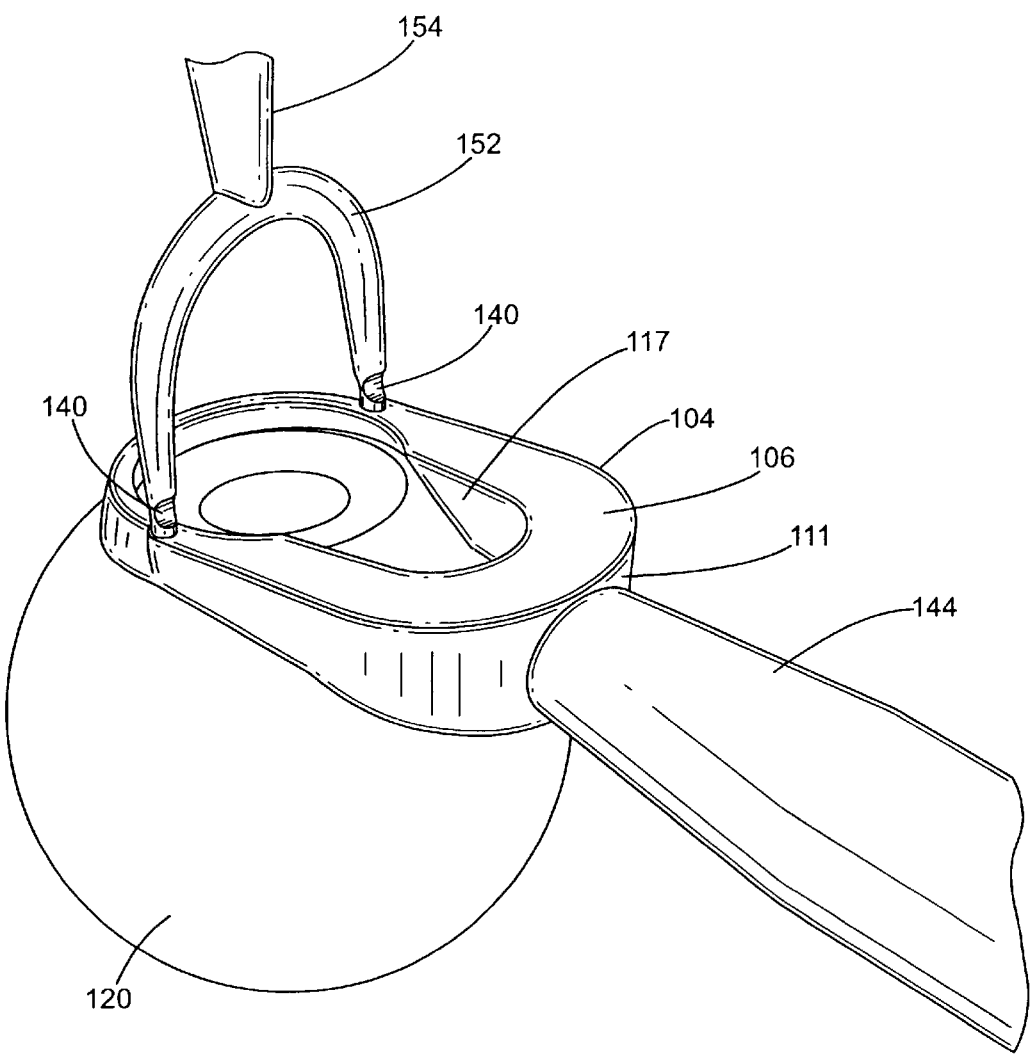
FIG. 17 is an enlarged perspective view of FIG. 13.

In FIGS. 17–19 aperture 142 further assists the blade in incising the eye at the fixed angle relative to the frame. Again, actuator 126 is preferably a plunger. However, as previously described as within the scope of the invention for the actuator to be other mechanisms.

Figure 21:
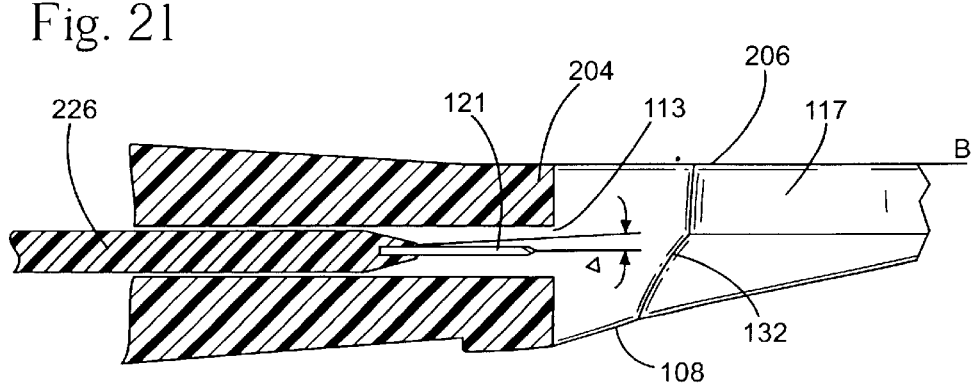
FIG. 21 is an enlarged cross sectional view taken along lines 21—21 in FIG. 20.

FIGS. 20–22 illustrate the function of corneal incision device 202 where frame 204 is being held in a selected position on the eye by use of vacuum 156 in addition to holding handle 236. For device 202 to function, frame 204 is placed over the eye in a selected position. Handle 236 is allowed to pivot to give access to the eye through hole 117. By applying distal motion on switch 160, a vacuum is created through frame 204 to apply suction to frame 204 to hold frame 204 in place. Further activation of actuator 226 and control switch 164 allows secondary vacuum source 162 to give further suction to frame 204 and actuator 226 advances the blade through aperture 113 to create the incision on the eye. Upon release of switch 160, control button 164 and actuator 226, biasing springs 180 provides proximal motion and return switch 160, control button 164, and actuator 226 back to their original position. When switch 160 and control button 164 return back to their original position the vacuum applied to the frame is seized and the frame is allowed to move. Upon return of actuator 226 to its original position, the blade is withdrawn into aperture 113 and the frame.

Corneal incision device 302 functions in a similar fashion. Upon distal force to actuator 326, the blade is advanced through aperture 113 to incise the eye at the fixed angle. Upon release of actuator 326 biasing spring 180 returns the actuator back to its original position and withdraws the blade into aperture 113 and frame 304.

The embodiments depicted in FIGS. 13–26 are intended to be merely exemplary and are not intended to depict all possible corneal incision devices. Rather, corneal incision devices 102 and its alternate embodiments device 202 and device 302 are to illustrate the present invention of greatly facilitating the ability to create an incision at the fixed angle on the eye by having a blade positioned at the fixed angle relative to the frame while having the frame in a secure selected position on the eye.

What is claimed is:

1. A corneal incision device for eye surgery comprising:
   a frame having a top, a bottom, and a side, said frame defining an aperture therein and having a hole to access the eye;
   a blade supported by said frame and positioned at a fixed angle relative to said frame; and
   an actuator attached to said blade for advancing and withdrawing said blade at said fixed angle through said aperture of said frame to create an incision on the eye, wherein said side of said frame further includes at least one handle to hold said frame on the eye with said handle having at least one pivot point to allow said handle to pivot about said frame.

2. The device of claim 1 wherein said bottom includes a surface contoured to the curvature of the eye and dimensioned to provide said fixed angle to said frame.

3. The device of claim 1 wherein said aperture is arcuate to create said fixed angle for said blade while advancing and withdrawing.

4. The device of claim 1 wherein said top further includes at least one handle to hold said frame on the eye.

5. The device of claim 1 wherein said actuator is a plunger rod.

6. The device of claim 1 wherein said frame further includes a housing fixedly attached to said side for protecting said blade.

7. A corneal incision device for eye surgery comprising:
a frame having a top, a bottom, and a side, said frame defining an aperture therein and having a hole to access the eye;
a blade supported by said frame and positioned at a fixed angle relative to said frame, said blade having a distal point having a beveled spear-shaped sharp tip;
a handle pivotably attached to said frame for holding said frame on the eye; and
an actuator attached to said blade for advancing and withdrawing said blade at said fixed angle through said aperture of said frame to create an incision on the eye.

8. The device of claim 7 wherein said handle is pivotably attached to said top.

9. The device in claim 7 wherein said handle is pivotably attached to said side.

10. The device in claim 7, wherein said handle further includes a fork portion and a stem portion such that said fork portion is disposed on said frame.

11. The device in claim 7 wherein said handle further includes a vacuum source connected to said frame and a switch to activate said vacuum source such that ambient air pressure retains said frame in a selected position on the eye as long as the vacuum source is applied.

12. The device in claim 11 wherein said frame further includes a secondary vacuum source and said actuator further includes at least one control button to control the activation of said blade and said secondary vacuum source.

13. The device in claim 7 wherein said actuator is a manually activated cantilever arm, a mechanical release including a bias spring, an electrical solenoid, a hydraulically activated mechanism, a pneumatically actuated mechanism, a vacuum actuated mechanism, a cam and cam follower, a cable release against a mechanical biasing spring, a plunger, a plunger against a biasing spring or combinations thereof.

14. The device in claim 13, wherein said actuator further includes a blade cartridge for holding said blade.

* * * * *